United States Patent
Furukawa et al.

(10) Patent No.: US 9,334,259 B2
(45) Date of Patent: May 10, 2016

(54) ARYLOXYACETAMIDE COMPOUND AND PESTICIDE

(71) Applicant: Nippon Soda Co., Ltd., Chiyoda-ku, Tokyo (JP)

(72) Inventors: Hironori Furukawa, Odawara (JP); Daisuke Hanai, Odawara (JP); Tetsuo Tamai, Odawara (JP); Yasuyuki Shiinoki, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 14/377,052

(22) PCT Filed: Feb. 12, 2013

(86) PCT No.: PCT/JP2013/053230
§ 371 (c)(1),
(2) Date: Aug. 6, 2014

(87) PCT Pub. No.: WO2013/122041
PCT Pub. Date: Aug. 22, 2013

(65) Prior Publication Data
US 2014/0364608 A1 Dec. 11, 2014

(30) Foreign Application Priority Data

Feb. 14, 2012 (JP) ................................. 2012-029731

(51) Int. Cl.
| | |
|---|---|
| C07D 401/12 | (2006.01) |
| A01N 43/40 | (2006.01) |
| A01N 43/54 | (2006.01) |
| C07D 215/20 | (2006.01) |
| C07D 239/26 | (2006.01) |
| C07D 417/12 | (2006.01) |
| C07C 381/10 | (2006.01) |
| C07D 213/40 | (2006.01) |
| C07D 213/68 | (2006.01) |
| A01N 41/06 | (2006.01) |
| A01N 43/42 | (2006.01) |
| A01N 43/78 | (2006.01) |
| C07D 213/56 | (2006.01) |
| C07D 277/62 | (2006.01) |

(52) U.S. Cl.
CPC .............. *C07D 401/12* (2013.01); *A01N 41/06* (2013.01); *A01N 43/40* (2013.01); *A01N 43/42* (2013.01); *A01N 43/54* (2013.01); *A01N 43/78* (2013.01); *C07C 381/10* (2013.01); *C07D 213/40* (2013.01); *C07D 213/56* (2013.01); *C07D 213/68* (2013.01); *C07D 215/20* (2013.01); *C07D 239/26* (2013.01); *C07D 277/62* (2013.01); *C07D 417/12* (2013.01)

(58) Field of Classification Search
CPC .................................................... C07D 401/12
See application file for complete search history.

(56) References Cited

FOREIGN PATENT DOCUMENTS

| | | |
|---|---|---|
| CN | 1192203 A | 9/1998 |
| JP | 05-070428 A | 3/1993 |
| JP | 2001-089758 A | 4/2001 |
| JP | 2005-517642 A | 6/2005 |
| JP | 2006-507338 A | 3/2006 |
| JP | 2006-507339 A | 3/2006 |
| WO | WO 96/39389 A1 | 12/1996 |
| WO | WO 02/49641 A2 | 6/2002 |
| WO | WO 02/50052 A1 | 6/2002 |
| WO | WO 03/048128 A1 | 6/2003 |
| WO | WO 2004/047537 A1 | 6/2004 |
| WO | WO 2004/047538 A1 | 6/2004 |
| WO | WO 2008/096231 A1 | 8/2008 |
| WO | WO 2010/118046 A1 | 10/2010 |
| WO | WO 2012/130917 A1 | 10/2012 |
| WO | WO 2012130917 A1 * | 10/2012 |
| WO | WO 2013/010082 A2 | 1/2013 |
| WO | WO 2013/010089 A2 | 1/2013 |

OTHER PUBLICATIONS

American Chemical Society. STN Database. RN 1326588-62-8.*
International Search Report dated May 21, 2013, in PCT/JP2013/053230.
Rit et al., "PD(II)-catalyzed Primary-C($sp^3$)-H Acyloxylation at Room Temperature," Organic Letters, 2012, 14(14):3724-3727.
STN on the Web, File Registry, RN=1326837-92-6, 1326588-62-8, 1326426-26-9, 1326021-57-1, 1324662-77-2, 1322350-66-2, 1301863-03-5, 1301695-46-4, 1301348-01-9, 1301345-44-7, 1301055-68-4, 1301055-52-6, 1299775-54-4, 1299096-28-8, 1298039-49-2, 1237824-67-9, 1296971-56-6, 1295620-85-7, 1294945-70-2, 1288354-70-0, 1278846-71-1, 1241649-93-3, 1197646-81-3, 1119376-70-3, 1026795-21-0, 941383-42-2, 316183-10-5, 316168-88-4, 316163-97-0, 316161-08-7, (c) 2015.
Office Action dated Aug. 10, 2015, in CN 201380008474.4, with partial English translation of search report.
Supplementary Partial European Search Report dated Jun. 23, 2015, in EP 13749513.1.
Aiello et al., "Discovery and Characterization of Inhibitors of *Pseudomonas aeruginosa* Type III Secretion," Antimicrobial Agents and Chemotherapy, Feb. 22, 2010, 54(5):1988-1999.

* cited by examiner

*Primary Examiner* — Noble Jarrell
*Assistant Examiner* — John S Kenyon
(74) *Attorney, Agent, or Firm* — Foley & Lardner LLP

(57) ABSTRACT

The present invention provides a pesticide comprising an aryloxyacetamide compound represented by formula (IV) (wherein in formula (IV), $R^{1a}$ represents an alkyl group or the like, $R^2$ to $R^5$ independently represents an alkyl group, X represents a halogen atom or the like, n represents an integer of 0 to 5, Z represents an oxygen atom or a sulfur atom) or salt thereof as an active ingredient.

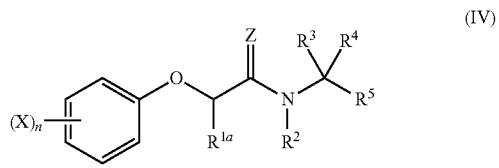

(IV)

8 Claims, No Drawings

ARYLOXYACETAMIDE COMPOUND AND PESTICIDE

TECHNICAL FIELD

The present invention relates to a novel pesticide. More specifically, the present invention relates to an aryloxyacetamide compound and an acaricide and/or insecticide containing the aryloxyacetamide compound as an active ingredient. The aryloxyacetamide compound has a superior acaricidal and/or insecticidal activity, superior safety, and can be synthesized advantageously and industrially.

CROSS-REFERENCE TO RELATED APPLICATIONS

This application is a National Stage application of PCT/JP2013/053230, filed Feb. 12, 2013, which claims priority from Japanese Patent Application No. 2012-29731, filed Feb. 14, 2012, the content of which is incorporated herein by reference.

BACKGROUND ART

Compounds represented by formulas (A) to (C), which are structurally relevant to the compound of the present invention, are disclosed in Patent documents 1 to 3.

[Chemical formula 1]

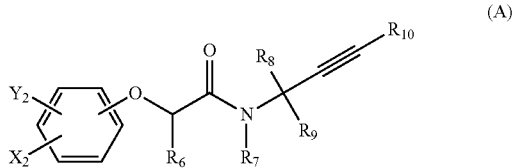

(A)

In formula (A), $X_2$ represents a hydrogen atom, halogen atom, C1-8 alkyl group or the like.

$Y_2$ represents a hydrogen atom, halogen atom, C1-8 alkyl group or the like.

$R_6$ represents a phenyl group, cyano group, C1-4 alkyl group or the like.

$R_7$ represents a hydrogen atom, C1-4 alkyl group or the like.

$R_8$ and $R_9$ independently represents a hydrogen atom, C1-3 alkyl group or the like.

$R_{10}$ represents a halogen atom or C1-4 alkyl group.

[Chemical formula 2]

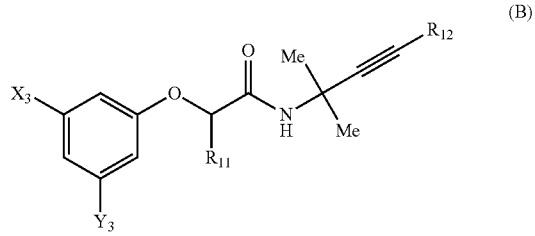

(B)

In formula (B), $X_3$ represents a chlorine atom, bromine atom, or methyl group.

$Y_3$ represents a chlorine atom, bromine atom, or methyl group.

$R_{11}$ represents an ethyl group or n-propyl group.

$R_{12}$ represents an ethyl group.

[Chemical formula 3]

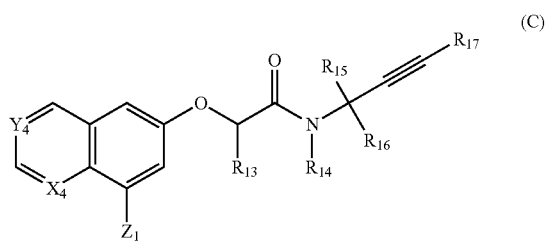

(C)

In formula (C), one of $X_4$ and $Y_4$ represents a nitrogen atom or nitrogen oxide, and the other one represents CR (wherein R represents a hydrogen atom, halogen atom or the like), or both $X_4$ and $Y_4$ represent a nitrogen atom.

$Z_1$ represents a hydrogen atom, halogen atom or the like.

$R_{13}$ represents an alkyl group, alkenyl group or the like.

$R_{14}$ represents a benzyloxymethyl group or the like, in which the phenyl ring of the benzyl moiety is optionally substituted with a C1-4 alkoxy group.

$R_{15}$ and $R_{16}$ do not simultaneously represent a hydrogen atom, and when both of them are not a hydrogen atom, they independently represents a hydrogen atom, C1-3 alkyl group or the like, provided that the number of carbon atoms of the combination of them does not exceed 4.

$R_{17}$ represents a C1-4 alkyl group, C3-6 cycloalkyl group or the like.

PRIOR ART LITERATURE

Patent Documents

Patent Document 1:
  Japanese Unexamined Patent Application Publication No. 2005-517642
Patent Document 2:
  Japanese Unexamined Patent Application Publication No. 2006-507338
Patent Document 3:
  Japanese Unexamined Patent Application Publication No. 2006-507339

DISCLOSURE OF INVENTION

Problems to be Solved by the Invention

The objective of the present invention is to provide a novel pesticide, particularly, to provide an aryloxyacetamide compound and an acaricide and/or insecticide containing the aryloxyacetamide compound as an active ingredient. The aryloxyacetamide compound has a superior acaricidal and/or insecticidal activity, superior safety, and can be synthesized advantageously and industrially.

Means for Solving the Problems

In order to achieve the above objective, the present inventors conducted extensive studies. As a result, the present inventors discovered that an aryloxyacetamide compound having a specific structure, or salt thereof, has a superior acaricidal and/or insecticidal activity, and may be used as an active ingredient of acaricides and/or insecticides having excellent properties and high safety.

The present invention was achieved on the basis of this perception.

Namely, the present invention is as follows:

(1) An aryloxyacetamide compound represented by formula (I), or salt thereof:

[Chemial formula 4]

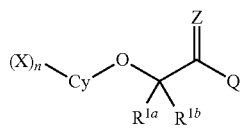

[in formula (I),

Cy represents a C6-10 aryl group, or a 5- to 10-membered heteroaryl group including 1 to 4 heteroatoms selected from the group consisting of a nitrogen atom, oxygen atom and sulfur atom.

X is a substituent of Cy, and represents an unsubstituted or substituted C1-6 alkyl group, unsubstituted or substituted C3-8 cycloalkyl group, unsubstituted or substituted C2-6 alkenyl group, unsubstituted or substituted C2-6 alkynyl group, hydroxy group, unsubstituted or substituted C1-6 alkoxy group, amino group, unsubstituted or substituted C1-6 alkyl amino group, unsubstituted or substituted C1-7 acyl group, unsubstituted or substituted C1-6 alkoxycarbonyl group, unsubstituted or substituted C1-6 alkyl thio group, unsubstituted or substituted C1-6 alkyl sulfonyl group, unsubstituted or substituted C1-6 alkoxysulfonyl group, unsubstituted or substituted C6-10 aryl group, 5- to 10-membered unsubstituted or substituted heteroaryl group including 1 to 4 heteroatoms selected from the group consisting of a nitrogen atom, oxygen atom and sulfur atom, unsubstituted or substituted hydroxyimino C1-6 alkyl group, nitro group, cyano group, or halogen atom.

n represents the number of X bonded with Cy and represents an integer of 0 to 5. When n is 2 or more, Xs may be the same as or different from each other. In addition, when n is 2 or more, Xs may bond to form a ring together with the carbon atoms or nitrogen atoms of Cy, which bond with Xs.

$R^{1a}$ represents an unsubstituted or substituted C1-6 alkyl group, unsubstituted or substituted C2-6 alkenyl group, unsubstituted or substituted C2-6 alkynyl group, unsubstituted or substituted C1-6 alkoxy group, or unsubstituted or substituted C1-6 alkyl thio group.

$R^{1b}$ represents a hydrogen atom, unsubstituted or substituted C1-6 alkyl group, unsubstituted or substituted C2-6 alkenyl group, or unsubstituted or substituted C2-6 alkynyl group. Here, $R^{1a}$ and $R^{1b}$ may bond to form a ring together with the carbon atom bonded thereto. Alternatively, $R^{1a}$ and $R^{1b}$ may together form an unsubstituted or substituted exomethylene group.

Z represents an oxygen atom or a sulfur atom.

Q represents a group represented by formula (II) or formula (III):

[Chemical formula 5]

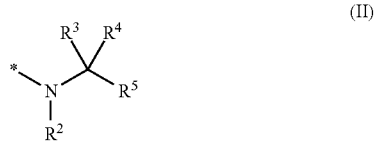

(in formula (II),

* represents bonding position.

$R^2$ represents a hydrogen atom, unsubstituted or substituted C1-6 alkyl group, unsubstituted or substituted C2-6 alkenyl group, unsubstituted or substituted C2-6 alkynyl group, unsubstituted or substituted C1-7 acyl group, or unsubstituted or substituted C1-6 alkoxycarbonyl group.

$R^3$ and $R^4$ independently represents an unsubstituted or substituted C1-6 alkyl group, unsubstituted or substituted C2-6 alkenyl group, unsubstituted or substituted C2-6 alkynyl group, unsubstituted or substituted C6-10 aryl group, 5- to 10-membered unsubstituted or substituted heteroaryl group including 1 to 4 heteroatoms selected from the group consisting of a nitrogen atom, oxygen atom and sulfur atom, or cyano group. Here, $R^3$ and $R^4$ may bond to form a ring together with the carbon atom bonded thereto.

$R^5$ represents a 5- to 10-membered unsubstituted or substituted heteroaryl group including 1 to 4 heteroatoms selected from the group consisting of a nitrogen atom, oxygen atom and sulfur atom.)

[Chemical formula 6]

(in formula (III),

* represents bonding position.

$R^6$ and $R^7$ independently represents an unsubstituted or substituted C1-6 alkyl group, unsubstituted or substituted C3-8 cycloalkyl group, unsubstituted or substituted C2-6 alkenyl group, unsubstituted or substituted C2-6 alkynyl group, unsubstituted or substituted C6-10 aryl group, or unsubstituted or substituted 5- to 10-membered heteroaryl group having at least 1 to 4 heteroatoms selected from the group consisting of a nitrogen atom, oxygen atom and sulfur atom. Here, $R^6$ and $R^7$ may bond to form a ring together with the sulfur atom bonded thereto.)]

(2) The aryloxyacetamide compound or salt thereof according to (1), wherein Cy represents a phenyl group, $R^{1b}$ represents a hydrogen atom, and Q represents a group represented by formula (II).

(3) A pesticide comprising at least one selected from the group consisting of the aryloxyacetamide compound and salt thereof defined in (1) or (2) as an active ingredient.

(4) An acaricide or insecticide comprising at least one selected from the group consisting of the aryloxyacetamide compound and salt thereof defined in (1) or (2) as an active ingredient.

(5) An ectoparasite control agent comprising at least one selected from the group consisting of the aryloxyacetamide compound and salt thereof defined in (1) or (2) as an active ingredient.

Effects of the Invention

The aryloxyacetamide compound or salt thereof according to the present invention is able to prevent pesticides which are harmful to agricultural crops or harmful in terms of hygiene. Particularly, the aryloxyacetamide compound or salt thereof according to the present invention is able to prevent acaricides effectively.

BEST MODE FOR CARRYING OUT THE INVENTION

[Aryloxyacetamide Compound]

The aryloxyacetamide compound of the present inventions is a compound represented by formula (I).

[Chemial formula 7]

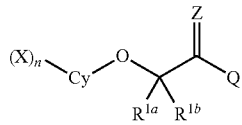

(I)

[Substituent]

In the present invention, the term "unsubstituted" refers to a group being the only group serving as a mother nucleus. In addition, in this description, when there is no description of being "substituted" and a description is only provided for the name of the group serving as a mother nucleus, this refers to "unsubstituted" unless specifically indicated otherwise.

On the other hand, the term "substituted" refers to any hydrogen atom or a group serving as a mother nucleus being substituted with a group having a structure that is the same as or different from the mother nucleus. Thus, a "substituent" is another group bonded with the group serving as the mother nucleus. There may be one substituent or two or more substituents. Two or more substituents may be the same as or different from each other.

The term "C1-6" or the like, for example, indicates that the number of carbon atoms of the group serving as the mother nucleus is 1 to 6. The number of carbon atoms present in substituents is not included in this number of carbon atoms. For example, a butyl group having an ethoxy group as a substituent thereof is classified as a C2 alkoxy C4 alkyl group.

The term "C1-6" or the like means that the base group has 1 to 6 carbon atoms. This number does not include the number of carbon atoms of the substituents. For example, a butyl group substituted with an ethoxy group is identified as a C2alkoxyC4 alkyl group.

The "substituent" is not particularly limited as long as it is chemically permissible and achieves the effects of the present invention.

Specific examples of the "substituent" include the following groups:

a halogen atom such as a fluorine atom, chlorine atom, bromine atom, iodine atom or the like;

a C1-6 alkyl group such as a methyl group, ethyl group, n-propyl group, i-propyl group, n-butyl group, s-butyl group, i-butyl group, t-butyl group, n-pentyl group, n-hexyl group or the like;

a C3-8 cycloalkyl group such as a cyclopropyl group, cyclobutyl group, cyclopentyl group, cyclohexyl group, cycloheptyl group or the like;

a C2-6 alkenyl group such as a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group, 5-hexenyl group or the like;

a C3-8 cycloalkenyl group such as a 2-cyclopropenyl group, 2-cyclopentenyl group, 3-cyclohexenyl group, 4-cyclooctenyl group or the like;

a C2-6 alkynyl group such as an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group, 1,1-dimethyl-2-butynyl group or the like;

a C1-6 alkoxy group such as a methoxy group, ethoxy group, n-propoxy group, i-propoxy group, n-butoxy group, s-butoxy group, i-butoxy group, t-butoxy group or the like;

a C2-6 alkenyloxy group such as a vinyloxy group, allyloxy group, propenyloxy group, butenyloxy group or the like;

a C2-6 alkynyloxy group such as an ethynyloxy group, propargyloxy group or the like;

a C6-10 aryl group such as a phenyl group, naphthyl group or the like;

a C6-10 aryloxy group such as a phenoxy group, 1-naphthoxy group or the like;

a C7-11 aralkyl group such as a benzyl group, phenethyl group or the like;

a C7-11 aralkyloxy group such as a benzyloxy group, phenethyloxy group or the like;

a C1-7 acyl group such as a formyl group, acetyl group, propionyl group, benzoyl group, cyclohexyl carbonyl group or the like;

a C1-7 acyloxy group such as a formyloxy group, acetyloxy group, propionyloxy group, benzoyloxy group, cyclohexyl carbonyloxy group or the like;

a C1-6 alkoxycarbonyl group such as a methoxycarbonyl group, ethoxycarbonyl group, n-propoxycarbonyl group, i-propoxycarbonyl group, n-butoxycarbonyl group, t-butoxycarbonyl group or the like;

a carboxyl group;

a hydroxy group;

a C1-6 haloalkyl group such as a chloromethyl group, chloroethyl group, trifluoromethyl group, 1,2-dichloro-n-propyl group, 1-fluoro-n-butyl group, perfluoro-n-pentyl group or the like;

a C2-6 haloalkenyl group such as a 2-chloro-1-propenyl group, 2-fluoro-1-butenyl group or the like;

a C2-6 haloalkynyl group such as a 4,4-dichloro-1-butynyl group, 4-fluoro-1-pentynyl group, 5-bromo-2-pentynyl group or the like;

a C1-6 haloalkoxy group such as a 2-chloro-n-propoxy group, 2,3-dichlorobutoxy group or the like;

a C2-6 haloalkenyloxy group such as a 2-chloropropenyloxy group, 3-bromobutenyloxy group or the like;

a C6-10 haloaryl group such as a 4-chlorophenyl group, 4-fluorophenyl group, 2,4-dichlorophenyl group or the like;

a C6-10 haloaryloxy group such as a 4-fluorophenyloxy group, 4-chloro-1-naphthoxy group or the like;

a halogen-substituted C1-7 acyl group such as a chloroacetyl group, trifluoroacetyl group, trichloroacetyl group, 4-chlorobenzoyl group or the like;

a cyano group; a nitro group; an amino group;

a C1-6 alkyl amino group such as a methyl amino group, dimethyl amino group, diethyl amino group or the like;

a C6-10 aryl amino group such as an anilino group, naphthyl amino group or the like;

a C7-11 aralkyl amino group such as a benzyl amino group, phenyl ethyl amino group or the like;

a C1-7 acyl amino group such as a formyl amino group, acetyl amino group, propanoyl amino group, butyryl amino group, i-propyl carbonyl amino group, benzoyl amino group or the like;

a C1-6 alkoxycarbonyl amino group such as a methoxycarbonyl amino group, ethoxycarbonyl amino group, n-propoxycarbonyl amino group, i-propoxycarbonyl amino group or the like;

an unsubstituted or substituted aminocarbonyl group such as an aminocarbonyl group, dimethyl aminocarbonyl group, phenyl aminocarbonyl group, N-phenyl-N-methyl aminocarbonyl group or the like;

an imino C1-6 alkyl group such as an iminomethyl group, (1-imino)ethyl group, (1-imino)-n-propyl group or the like;

a hydroxyimino C1-6 alkyl group such as a hydroxyiminomethyl group, (1-hydroxyimino)ethyl group, (1-hydroxyimino)propyl group or the like;

a mercapto group;

a C1-6 alkyl thio group such as a methyl thio group, ethyl thio group, n-propyl thio group, i-propyl thio group, n-butyl thio group, i-butyl thio group, s-butyl thio group, t-butyl thio group or the like;

a C2-6 alkenyl thio group such as a vinyl thio group, allyl thio group or the like;

a C2-6 alkynyl thio group such as an ethynyl thio group, propargyl thio group or the like;

a C6-10 aryl thio group such as a phenyl thio group, naphthyl thio group or the like;

a heteroaryl thio group such as a thiazolyl thio group, pyridyl thio group or the like;

a C7-11 aralkyl thio group such as a benzyl thio group, phenethyl thio group or the like;

a (C1-6 alkyl thio)carbonyl group such as a (methyl thio)carbonyl group, (ethyl thio)carbonyl group, (n-propyl thio)carbonyl group, (i-propyl thio)carbonyl group, (n-butyl thio)carbonyl group, (i-butyl thio)carbonyl group, (s-butyl thio)carbonyl group, (t-butyl thio)carbonyl group or the like;

a C1-6 alkyl sulfinyl group such as a methyl sulfinyl group, ethyl sulfinyl group, t-butyl sulfinyl group or the like;

a C2-6 alkenyl sulfinyl group such as an allyl sulfinyl group or the like;

a C2-6 alkynyl sulfinyl group such as a propargyl sulfinyl group or the like;

a C6-10 aryl sulfinyl group such as a phenyl sulfinyl group or the like;

a heteroaryl sulfinyl group such as a thiazolyl sulfinyl group, pyridyl sulfinyl group or the like;

a C7-11 aralkyl sulfinyl group such as a benzyl sulfinyl group, phenethyl sulfinyl group or the like;

a C1-6 alkyl sulfonyl group such as a methyl sulfonyl group, ethyl sulfonyl group, t-butyl sulfonyl group or the like;

a C2-6 alkenyl sulfonyl group such as an allyl sulfonyl group or the like;

a C2-6 alkynyl sulfonyl group such as a propargyl sulfonyl group or the like;

a C6-10 aryl sulfonyl group such as a phenyl sulfonyl group or the like;

a heteroaryl sulfonyl group such as a thiazolyl sulfonyl group, pyridyl sulfonyl group or the like;

a C7-11 aralkyl sulfonyl group such as a benzyl sulfonyl group, phenethyl sulfonyl group or the like;

a 5-membered heteroaryl group such as a pyrrolyl group, furyl group, thienyl group, imidazolyl group, pyrazolyl group, oxazolyl group, isoxazolyl group, thiazolyl group, isothiazolyl group, triazolyl group, oxadiazolyl group, thiadiazolyl group, tetrazolyl group or the like;

a 6-membered heteroaryl group such as a pyridyl group, pyrazinyl group, pyrimidinyl group, pyridazinyl group, triazinyl group or the like;

a condensed heteroaryl group such as an indolyl group, benzofuryl group, benzothienyl group, benzimidazolyl group, benzoxazolyl group, benzothiazolyl group, quinolyl group, isoquinolyl group, quinoxalinyl group or the like;

a saturated heterocyclic group such as an aziridinyl group, oxiranyl group, pyrrolidinyl group, tetrahydrofuranyl group, piperidyl group, piperazinyl group, morpholinyl group or the like;

a tri C1-6 alkyl-substituted silyl group such as a trimethyl silyl group, triethyl silyl group, t-butyl dimethyl silyl group or the like;

a triphenyl silyl group or the like; and the like.

In addition, these "substituents" may be substituted with other "substituents".

[Cy]

In formula (I), Cy represents a C6-10 aryl group or a heteroaryl group.

The "C6-10 aryl group" may be a monocyclic ring, or a polycyclic ring in which the rings bond with each other. In the polycyclic aryl group, as long as at least one aromatic ring is included, other rings may be a saturated alicyclic ring, an unsaturated alicyclic ring or an aromatic ring. Examples of the C6-10 aryl group include a phenyl group, naphthyl group, azulenyl group, indenyl group, indanyl group, tetralinyl group or the like.

The "heteroaryl group" is a 5- to 10-membered aryl group which has, other than carbon atoms, 1 to 4 heteroatoms selected from the group consisting of a nitrogen atom, oxygen atom and sulfur atom as the atoms constituting the ring. The heteroaryl group may be a monocyclic ring, or a polycyclic ring in which the rings bond to each other.

Examples of the heteroaryl group include a 5-membered heteroaryl group, 6-membered heteroaryl group, condensed heteroaryl group or the like, which are listed as the examples of the "substituent".

Among these groups, Cy is preferably a phenyl group, naphthyl group, pyridyl group, pyrimidinyl group, pyridazinyl group, indolyl group, benzofuryl group, benzothienyl group, benzimidazolyl group, benzoxazolyl group, benzothiazolyl group, quinolyl group, isoquinolyl group, or quinoxalinyl group, and more preferably a phenyl group.

[X]

In formula (I), X represents a substituent of Cy, X represents an unsubstituted or substituted C1-6 alkyl group, unsubstituted or substituted C3-8 cycloalkyl group, unsubstituted or substituted C2-6 alkenyl group, unsubstituted or substituted C2-6 alkynyl group, hydroxy group, unsubstituted or substituted C1-6 alkoxy group, amino group, unsubstituted or substituted C1-6 alkyl amino group, unsubstituted or substituted C1-7 acyl group, unsubstituted or substituted C1-6 alkoxycarbonyl group, unsubstituted or substituted C1-6 alkyl thio group, unsubstituted or substituted C1-6 alkyl sulfonyl group, unsubstituted or substituted C1-6 alkoxysulfonyl group, unsubstituted or substituted C6-10 aryl group, unsubstituted or substituted heteroaryl group, unsubstituted or substituted hydroxyimino C1-6 alkyl group, nitro group, cyano group, or halogen atom.

n represents the number of X of Cy, and represents an integer of 0 to 5. When n is 2 or more, Xs may the same as or different from each other. In addition, when X is 2 or more, Xs may bond to form a ring together with the carbon atoms or nitrogen atoms, which bond with Xs.

The "C1-6 alkyl group" of X may be a linear alkyl group or a branched alkyl group. Examples of the alkyl group include a methyl group, ethyl group, n-propyl group, n-butyl group, n-pentyl group, n-hexyl group, i-propyl group, i-butyl group, s-butyl group, t-butyl group, i-pentyl group, neopentyl group, 2-methyl butyl group, 2,2-dimethyl propyl group, i-hexyl group or the like.

Examples of the "substituted C1-6 alkyl group" include a C3-8 cycloalkyl C1-6 alkyl group such as a cyclopropyl methyl group, 2-cyclopropyl ethyl group, cyclopentyl methyl group, 2-cyclohexyl ethyl group, 2-cyclooctyl ethyl group or the like;

a C1-6 haloalkyl group such as a fluoromethyl group, chloromethyl group, bromomethyl group, difluoromethyl group, dichloromethyl group, dibromomethyl group, trifluoromethyl group, trichloromethyl group, tribromomethyl group, 2,2,2-tolufluoroethyl group, 2,2,2-trichloroethyl group, pentafluoroethyl group, 4-fluorobutyl group, 4-chlorobutyl group, 3,3,3-trifluoropropyl group, 2,2,2-trifluoro-1-trifluoromethyl ethyl group, perfluorohexyl group, perchlorohexyl group, 2,4,6-trichlorohexyl group or the like;

a hydroxy C1-6 alkyl group such as a hydroxymethyl group, 2-hydroxyethyl group or the like;

a C1-6 alkoxy C1-6 alkyl group such as a methoxymethyl group, ethoxymethyl group, methoxyethyl group, ethoxyethyl group, methoxy-n-propyl group, ethoxymethyl group, ethoxyethyl group, n-propoxymethyl group, i-propoxyethyl group, s-butoxymethyl group, t-butoxyethyl group or the like;

a C2-6 alkenyloxy C1-6 alkyl group such as a vinyloxymethyl group, allyloxymethyl group, propenyloxymethyl group, butenyloxymethyl group or the like;

a heteroaryloxy C1-6 alkyl group such as a pyridine-2-yloxymethyl group or the like;

a C1-7 acyl group such as a formyl group, acetyl group, propionyl group or the like;

a C1-7 acyloxy C1-6 alkyl group such as a formyloxymethyl group, acetoxymethyl group, 2-acetoxyethyl group, propionyloxymethyl group, propionyloxyethyl group or the like;

a carboxyl group C1-6 alkyl group such as a carboxyl methyl group, carboxyl ethyl group or the like;

a C1-6 alkoxycarbonyl C1-6 alkyl group such as a methoxycarbonyl methyl group, ethoxycarbonyl methyl group, n-propoxycarbonyl methyl group, i-propoxycarbonyl methyl group or the like;

a C1-7 acyl amino C1-6 alkyl group such as a formamide methyl group, acetamide methyl group, 2-acetamide ethyl group, propionyl aminomethyl group, propionyl aminoethyl group or the like;

a C1-6 alkyl aminocarbonyl C1-6 alkyl group such as a methyl aminocarbonyl methyl group, ethyl aminocarbonyl methyl group, i-propyl aminocarbonyl methyl group, t-butyl aminocarbonyl methyl group, s-butyl aminocarbonyl methyl group, n-pentyl aminocarbonyl methyl group or the like;

a C1-6 alkoxycarbonyl amino C1-6 alkyl group such as a methoxycarbonyl aminomethyl group, ethoxycarbonyl aminomethyl group, i-propoxycarbonyl aminomethyl group, t-butoxycarbonyl aminomethyl group, s-butyloxycarbonyl aminomethyl group, n-pentyloxycarbonyl aminomethyl group or the like;

a C7-11 aralkyl group such as a benzyl group, phenethyl group or the like;

a C6-10 aryl carbonyl amino C1-6 alkyl group such as a benzoyl aminomethyl group or the like; and the like.

Examples of the "C3-8 cycloalkyl group" of X include a cyclopropyl group, cyclobutyl group, cyclopentyl group, cyclohexyl group, cycloheptyl group and the like.

Examples of the "C2-6 alkenyl group" of X include a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group, 5-hexenyl group and the like.

Examples of the "substituted C2-6 alkenyl group" include a C2-6 haloalkenyl group and the like, such as a 2-chloro-1-propenyl group, 2-fluoro-1-butenyl group or the like.

Examples of "C2-6 alkynyl group" of X include an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group, 1,1-dimethyl-2-butynyl group and the like.

Examples of the "substituted C2-6 alkynyl group" include a C2-6 haloalkynyl group and the like, such as a 4,4-dichloro-1-butynyl group, 4-fluoro-1-pentynyl group, 5-bromo-2-pentynyl group or the like.

Examples of the "C1-6 alkoxy group" of X include a methoxy group, ethoxy group, n-propoxy group, n-butoxy group, n-pentyloxy group, n-hexyloxy group, i-propoxy group, i-butoxy group, s-butoxy group, t-butoxy group, i-hexyloxy group and the like.

Examples of the "substituted C1-6 alkoxy group" include a C1-6 haloalkoxy group and the like, such as a chloromethoxy group, dichloromethoxy group, difluoromethoxy group, trichloromethoxy group, trifluoromethoxy group, 1-fluoroethoxy group, 1,1-difluoroethoxy group, 2,2,2-trifluoroethoxy group, pentafluoroethoxy group or the like.

Examples of the "C1-6 alkylamino group" of X include a methyl amino group, dimethyl amino group, diethyl amino group and the like.

Examples of the "C1-7 acyl group" of X include a formyl group, acetyl group, propionyl group, benzoyl group and the like.

Examples of the "substituted C1-7 acyl group" include a halogen-substituted C1-7 acyl group and the like, such as a chloroacetyl group, trifluoroacetyl group, trichloroacetyl group, 4-chlorobenzoyl group or the like.

Examples of the "C1-6 alkoxycarbonyl group" of X include a methoxycarbonyl group, ethoxycarbonyl group, n-propoxycarbonyl group, i-propoxycarbonyl group and the like.

Examples of the "substituted C1-6 alkoxycarbonyl group" include a C3-8 cycloalkyl C1-6 alkoxycarbonyl group such as a cyclopropyl methoxycarbonyl group, cyclobutyl methoxycarbonyl group, cyclopentyl methoxycarbonyl group, cyclohexyl methoxycarbonyl group, 2-methyl cyclopropyl methoxycarbonyl group, 2,3-dimethyl cyclopropyl methoxycarbonyl group, 2-chlorocyclopropyl methoxycarbonyl group, 2-cyclopropyl ethoxycarbonyl group or the like;

a C1-6 haloalkoxycarbonyl group such as a fluoromethoxycarbonyl group, chloromethoxycarbonyl group, bromomethoxycarbonyl group, difluoromethoxycarbonyl group, dichloromethoxycarbonyl group, dibromomethoxycarbonyl group, trifluoromethoxycarbonyl group, tri chloromethoxycarbonyl group, tribromomethoxycarbonyl group, 2,2,2-trifluoroethoxycarbonyl group, 2,2,2-trichloroethoxycarbonyl group, pentafluoroethoxycarbonyl group, 4-fluorobutoxycarbonyl group, 3,3,3-trifluoropropoxycarbonyl group, 2,2,2-trifluoro-1-trifluoromethyl ethoxycarbonyl group, perfluorohexyloxycarbonyl group or the like; and the like.

Examples of the "C1-6 alkylthio group" of X include a methyl thio group, ethyl thio group, n-propyl thio group, n-butyl thio group, n-pentyl thio group, n-hexyl thio group, i-propyl thio group or the like.

Examples of the "substituted C1-6 alkylthio group" include a C1-6 haloalkyl thio group and the like, such as a trifluoromethyl thio group, 2,2,2-tolufluoroethyl thio group and the like.

Examples of the "C1-6 alkyl sulfonyl group" of X include a methyl sulfonyl group, ethyl sulfonyl group, t-butyl sulfonyl group and the like.

Examples of the "substituted C1-6 alkyl sulfonyl group" include a C1-6 haloalkylsulfonyl group and the like, such as a trifluoromethyl sulfonyl group, 2,2,2-tolufluoroethyl sulfonyl group or the like.

Examples of the "C1-6 alkoxysulfonyl group" of X include a methoxysulfonyl group, ethoxysulfonyl group, t-butoxysulfonyl group and the like.

Examples of the "C6-10 aryl group" and "heteroaryl group" of X are the same as the examples of Cy.

Examples of the "C6-10 aryl group" and "heteroaryl group" of X include
a halogen atom such as a fluorine atom, chlorine atom, bromine atom, iodine atom or the like;
a C1-6 alkyl group such as a methyl group, ethyl group, n-propyl group, i-propyl group, n-butyl group, s-butyl group, i-butyl group, t-butyl group, n-pentyl group, n-hexyl group or the like;
a C1-6 haloalkyl group such as a chloromethyl group, chloroethyl group, trifluoromethyl group, 1,2-dichloro-n-propyl group, 1-fluoro-n-butyl group, perfluoro-n-pentyl group or the like;
a cyano group; and the like.

Examples of the "hydroxyimino C1-6 alkyl group" of X include a hydroxyiminomethyl group, (1-hydroxyimino) ethyl group, (1-hydroxyimino)propyl group and the like.

Examples of the "substituted hydroxyimino C1-6 alkyl group" include a C1-6 alkoxyimino C1-6 alkyl group such as a methoxyiminomethyl group, (1-methoxyimino)ethyl group, (1-methoxyimino)propyl group, ethoxyiminomethyl group, (1-ethoxyimino)ethyl group, (1-ethoxyimino)propyl group or the like; a C3-8 cycloalkyl C1-6 alkoxyimino C1-6 alkyl group such as a (1-cyclopropyl methoxyimino)ethyl group or the like; a C7-11 aralkyloxyimino C1-6 alkyl group such as a benzyloxyiminomethyl group, (1-benzyloxyimino) ethyl group or the like; and the like.

Examples of the "halogen atom" of X include a fluorine atom, chlorine atom, bromine atom, iodine atom and the like.

Examples of the ring formed by bonding Xs together with the carbon atoms or nitrogen atoms bonded thereto include a cyclopentene ring, cyclohexene ring, 3,4-dihydro-2H-pyran ring, 3,4-dihydro-2H-thiopyran ring, 3,4-dihydro-2H-thiopyran 1,1-dioxide ring and the like.

[$R^{1a}$]

In formula (I), $R^{1a}$ represents an unsubstituted or substituted C1-6 alkyl group, unsubstituted or substituted C2-6 alkenyl group, unsubstituted or substituted C2-6 alkynyl group, unsubstituted or substituted C1-6 alkoxy group, or unsubstituted or substituted C1-6 alkyl thio group.

Examples of the "C1-6 alkyl group", "C2-6 alkenyl group", "C2-6 alkynyl group", "C1-6 alkoxy group" and "C1-6 alkyl thio group" of $R^{1a}$ are the same as the examples of X described above.

$R^{1a}$ is preferably a C1-6 alkyl group.

[$R^{1b}$]

In formula (I), $R^{1b}$ represents a hydrogen atom, unsubstituted or substituted C1-6 alkyl group, unsubstituted or substituted C2-6 alkenyl group, or unsubstituted or substituted C2-6 alkynyl group. Here, $R^{1a}$ and $R^{1b}$ may bond to form a ring together with the carbon atom bonded thereto.

Examples of the "unsubstituted or substituted C1-6 alkyl group", "unsubstituted or substituted C2-6 alkenyl group", and "unsubstituted or substituted C2-6 alkynyl group" of $R^{1b}$ are the same as the examples of X described above.

Examples of the ring formed by bonding $R^{1a}$ and $R^{1b}$ together with the carbon atom bonded thereto include a cyclopropane ring, cyclobutane ring, cyclopentane ring, cyclohexane ring, cycloheptane ring and the like.

Examples of the "substituted exomethylene group" formed by $R^{1a}$ and $R^{1b}$ together with the carbon atom bonded thereto include a C1-6 alkyl-substituted exomethylene such as an ethylidene group, isopropylidene group or the like.

[Q]

In formula (I), Q represents a group represented by formula (II) or formula (III).

[Chemical formula 8]

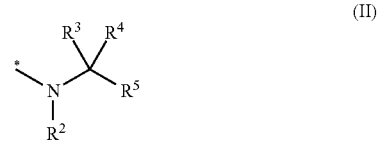

In formula (II), * represents bonding position.

[$R^2$]

In formula (II), $R^2$ represents a hydrogen atom, unsubstituted or substituted C1-6 alkyl group, unsubstituted or substituted C2-6 alkenyl group, unsubstituted or substituted C2-6 alkynyl group, unsubstituted or substituted C1-7 acyl group, or unsubstituted or substituted C1-6 alkoxycarbonyl group.

Examples of the "unsubstituted or substituted C1-6 alkyl group", "unsubstituted or substituted C2-6 alkenyl group", "unsubstituted or substituted C2-6 alkynyl group", "unsubstituted or substituted C1-7 acyl group", and "unsubstituted or substituted C1-6 alkoxycarbonyl group" of $R^2$ are the same as the examples of X described above.

[$R^3$, $R^4$]

In formula (II), $R^3$ and $R^4$ independently represents an unsubstituted or substituted C1-6 alkyl group, unsubstituted or substituted C2-6 alkenyl group, unsubstituted or substituted C2-6 alkynyl group, unsubstituted or substituted C6-10 aryl group, unsubstituted or substituted heteroaryl group, or cyano group. Here, $R^3$ and $R^4$ may bond to form a ring together with the carbon atom bonded thereto.

Examples of the "unsubstituted or substituted C1-6 alkyl group", "unsubstituted or substituted C2-6 alkenyl group", and "unsubstituted or substituted C2-6 alkynyl group" of $R^3$ and $R^4$ are the same as the examples of X described above.

Examples of the "unsubstituted or substituted C6-10 aryl group" and "unsubstituted or substituted heteroaryl group" of $R^3$ and $R^4$ are the same as the examples of Cy.

$R^3$ and $R^4$ are preferably a C1-6 alkyl group.

The ring formed by bonding $R^3$ and $R^4$ together with the atom bonded thereto includes a cyclopropane ring, cyclobutane ring, cyclopentane ring, cyclohexane ring, oxirane ring and the like.

[$R^5$]

$R^5$ represents an unsubstituted or substituted heteroaryl group.

Examples of the "heteroaryl group" of $R^5$ include a 5-membered heteroaryl group such as a pyrrolyl group, furyl group, thienyl group, imidazolyl group, pyrazolyl group, oxazolyl group, isoxazolyl group, thiazolyl group, isothiazolyl group, triazolyl group, oxadiazolyl group, thiadiazolyl group, tetrazolyl group or the like;

a 6-membered heteroaryl group such as a pyridyl group, pyrazinyl group, pyrimidinyl group, pyridazinyl group, triazinyl group or the like;

a condensed heteroaryl group such as an indolyl group, benzofuryl group, benzothienyl group, benzimidazolyl group, benzoxazolyl group, benzothiazolyl group, quinolyl group, isoquinolyl group, quinoxalinyl group or the like;

a partially unsaturated 5-membered heterocyclic group such as a pyrrolinyl group, imidazolinyl group, pyrazolinyl group, oxazolinyl group, thiazolinyl group or the like; and the like.

As the "heteroaryl group" of $R^5$, a pyridyl group is preferable.

Examples of the substituents of the "substituted heteroaryl group" of $R^5$ include the following substituents:

a halogen atom such as a fluorine atom, chlorine atom, bromine atom, iodine atom or the like;

a C1-6 alkyl group such as a methyl group, ethyl group, n-propyl group, i-propyl group, n-butyl group, s-butyl group, i-butyl group, t-butyl group, n-pentyl group, n-hexyl group or the like;

a C3-8 cycloalkyl group such as a cyclopropyl group, cyclobutyl group, cyclopentyl group, cyclohexyl group, cycloheptyl group or the like;

a C2-6 alkenyl group such as a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group, 5-hexenyl group or the like;

a C2-6 alkynyl group such as a ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group, 1,1-dimethyl-2-butynyl group or the like;

a C1-6 alkoxy group such as a methoxy group, ethoxy group, n-propoxy group, i-propoxy group, n-butoxy group, s-butoxy group, i-butoxy group, t-butoxy group or the like;

a C6-10 aryl group such as a phenyl group, naphthyl group or the like;

a C1-6 haloalkyl group such as a chloromethyl group, chloroethyl group, trifluoromethyl group, 1,2-dichloro-n-propyl group, 1-fluoro-n-butyl group, perfluoro-n-pentyl group or the like;

a C6-10 haloaryl group such as a 4-chlorophenyl group, 4-fluorophenyl group, 2,4-dichlorophenyl group or the like;

a cyano group; a nitro group;

a 5-membered heteroaryl group such as a pyrrolyl group, furyl group, thienyl group, imidazolyl group, pyrazolyl group, oxazolyl group, isoxazolyl group, thiazolyl group, isothiazolyl group, triazolyl group, oxadiazolyl group, thiadiazolyl group, tetrazolyl group or the like;

a 6-membered heteroaryl group such as a pyridyl group, pyrazinyl group, pyrimidinyl group, pyridazinyl group, triazinyl group or the like;

[Chemical formula 9]

(III)

In formula (III), * represents bonding position.

[$R^6$, $R^7$]

In formula (III), $R^6$ and $R^7$ independently represents an unsubstituted or substituted C1-6 alkyl group, unsubstituted or substituted C3-8 cycloalkyl group, unsubstituted or substituted C2-6 alkenyl group, unsubstituted or substituted C2-6 alkynyl group, unsubstituted or substituted C6-10 aryl group, or unsubstituted or substituted heteroaryl group. Here, $R^6$ and $R^7$ may bond to form a ring together with the sulfur atom bonded thereto.

Examples of the "unsubstituted or substituted C1-6 alkyl group", "unsubstituted or substituted 3-8 cycloalkyl group", "unsubstituted or substituted C2-6 alkenyl group", and "unsubstituted or substituted C2-6 alkynyl group" of $R^6$ and $R^7$ are the same as the examples of X described above.

Examples of the "unsubstituted or substituted C6-10 aryl group" and "unsubstituted or substituted heteroaryl group" of $R^6$ and $R^7$ are the same as the examples of Cy describe above.

Examples of the substituents of the "substituted C6-10 aryl group" and "substituted heteroaryl group" of $R^6$ and $R^7$ include a halogen atom fluorine atom, chlorine atom, bromine atom, iodine atom or the like;

a C1-6 alkyl group methyl group, ethyl group, n-propyl group, i-propyl group, n-butyl group, s-butyl group, i-butyl group, t-butyl group, n-pentyl group, n-hexyl group or the like;

a C1-6 haloalkyl group chloromethyl group, chloroethyl group, trifluoromethyl group, 1,2-dichloro-n-propyl group, 1-fluoro-n-butyl group, perfluoro-n-pentyl group or the like;

a cyano group; and the like.

Examples of the ring formed by bonding $R^6$ and $R^7$ together with the sulfur atom bonded thereto include a tetrahydrothiophene ring, tetrahydrothiopyran ring, oxathiane ring and the like.

[Z]

In formula (I), Z represents an oxygen atom or sulfur atom, and preferably represents an oxygen atom.

[Aryloxyacetamide Compound Represented by Formula (IV)]

Among the aryloxyacetamide compounds of the present invention, a compound wherein Cy in formula (I) represents a phenyl group, $R^{1b}$ in formula (I) represents a hydrogen atom, and Q represents a group represented by formula (II), is preferable. That is, an aryloxyacetamide compound represented by formula (IV) is preferable.

[Chemical formula 10]

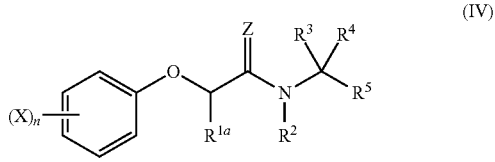

In formula (IV), $R^{1a}$, $R^2$-$R^5$, X, n, and Z are as defined in formula (I) and formula (II).

[Salt of the Aryloxyacetamide Compound]

There are no particular limitations on the salt of the compound of the present invention provided it is an agriculturally and horticulturally allowable salt. Examples of the salt include salts of inorganic acids such as hydrochloric acid or sulfuric acid; salts of organic acids such as acetic acid or lactic acid; salts of alkaline metals such as lithium, sodium or potassium; salts of alkaline earth metals such as calcium or magnesium; salts of transition metals such as iron or copper; and, salts of organic bases such as ammonia, triethylamine, tributylamine, pyridine or hydrazine. The salts of the aryloxyacetamide compound can be produced by generally-known methods.

[Production Method]

Next, the following provides an explanation of a production method of the aryloxyacetamide compound of the present invention.

1) As an example of the production method, the following scheme is exemplified.

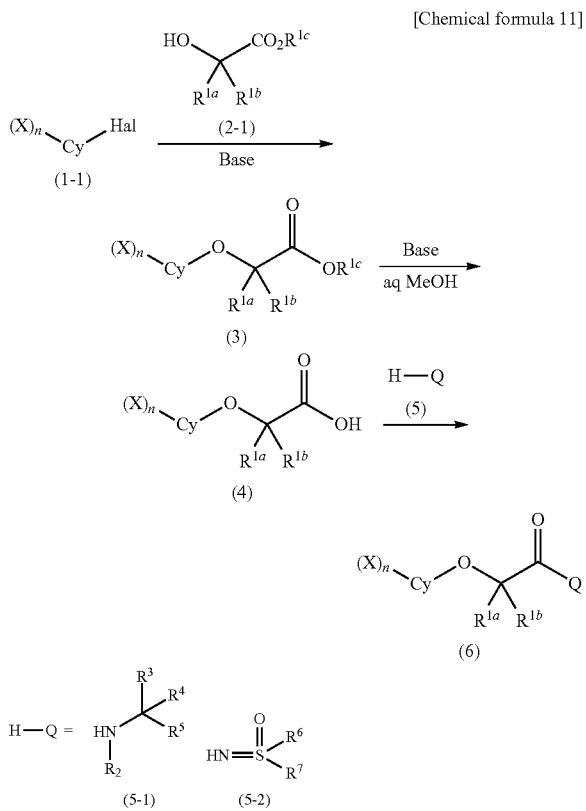

a) An aryloxyacetate compound represented by formula (3) (hereinafter, may be referred to as "compound (3)") is obtained by reacting a haloaryl compound represented by formula (1-1) (hereinafter, may be referred to as "compound (1-1)") with an ester compound represented by formula (2-1) (hereinafter, may be referred to as "compound (2-1)") in the presence of a base. Next, an aryloxyacetic acid compound represented by formula (4) (hereinafter, may be referred to as "compound (4)") is produced by hydrolyzing the resulting compound (3).

In formula (1-1), formula (2-1), formula (3) and formula (4), X, n, $R^{1a}$, $R^{1b}$ and Cy are as defined as above. In formula (1-1), Hal represents a halogen atom. In formula (2-1), $R^{1c}$ represents a C1-6 alkyl group.

The amount of compound (2-1) is generally 1 to 2 mol, and preferably 1.0 to 1.2 mol with respect to 1 mol of compound (1-1).

Although the reaction may be performed in the absence of a base, it is preferable to perform the reaction in the presence of a base. Examples of the base include pyridine, triethylamine, potassium hydroxide and the like. The amount of the base is generally 1 to 2 mol with respect to 1 mol of compound (1-1).

The reaction may be performed in a solvent. There are no particular limitations on the solvent provided it is inactive against the reaction. Examples of the solvent include ether type solvents such as dioxane, 1,2-dimethoxyethane, tetrahydrofuran; aromatic hydrocarbon type solvents such as toluene, benzene, xylene; aliphatic hydrocarbon type solvents such as n-pentane, n-hexane, n-heptane; halogenated hydrocarbon type solvents such as dichloromethane, chloroform, carbon tetrachloride, 1,2-dichloroethane; amide type solvents such as N,N-dimethyl formamide, N,N-dimethyl acetamide, N-methyl pyrrolidone; nitrile type solvents such as acetonitrile, benzonitrile; and mixed solvents including two or more of these solvents; and the like. Although there are no particular limitations on the amount of the solvent, it is generally 1 to 100 ml with respect to 1 g of compound (1-1).

The reaction temperature ranges from −20° C. to the boiling point of the solvent. Although the reaction time varies according to the reaction scale, it is generally from minutes to hours.

Next, although the hydrolysis can be performed by ordinary methods, it is preferable to perform in the presence of a base. Examples of the base include a metal hydroxide and the like, such as lithium hydroxide, sodium hydroxide, potassium hydroxide, sodium carbonate, potassium carbonate or the like. The amount of the base is generally 1 to 20 mol with respect to 1 mol of compound (3).

The reaction may be performed in a solvent. There are no particular limitations on the solvent provided it is miscible with water and inactive against the reaction. Examples of the solvent are the same as the examples of the solvent used for producing compound (2). Although there are no particular limitations on the amount of the solvent, it is generally 1 to 100 ml with respect to 1 g of compound (3).

The reaction temperature ranges from room temperature to the boiling point of the solvent. Although the reaction time varies according to the reaction scale, it is generally from minutes to hours.

b) An aryloxyacetamide compound represented by formula (6) (hereinafter, may be referred to as "compound (6)") is produced by reacting compound (4) with a compound represented by formula (5) (hereinafter, may be referred to as "compound (5)"). Here, compound (5) is an amine compound represented by formula (5-1) (hereinafter, may be referred to as "compound (5-1)") or a sulfoximine compound represented by formula (5-2) (hereinafter, may be referred to as "compound (5-2)").

In addition, in formula (5), Q is as defined above. In formula (6), X, n, $R^{1a}$, $R^{1b}$ and Cy are as defined above. In formula (5-1) and formula (5-2), $R^2$ to $R^8$ are as defined above.

The amount of compound (5) is generally 1 to 2 mol, and preferably 1.0 to 1.2 mol with respect to 1 mol of compound (4).

The reaction may be performed in a solvent. There are no particular limitations on the solvent provided it is inactive against the reaction. Examples of the solvent are the same as the examples of the solvent used for producing compound (2). Although there are no particular limitations on the amount of the solvent, it is generally 1 to 100 ml with respect to 1 g of compound (4).

In addition, when performing a reaction with compound (5-2), it is preferable to perform in the presence of a base. Examples of the base include pyridine, triethylamine, potassium hydroxide and the like. The amount of the base is generally 1 to 2 mol with respect to 1 mol of compound (4).

The reaction temperature ranges from room temperature to the boiling point of the solvent. Although the reaction time varies according to the reaction scale, it is generally from minutes to hours.

2) As another example of the production method of compound (3), the following scheme is exemplified.

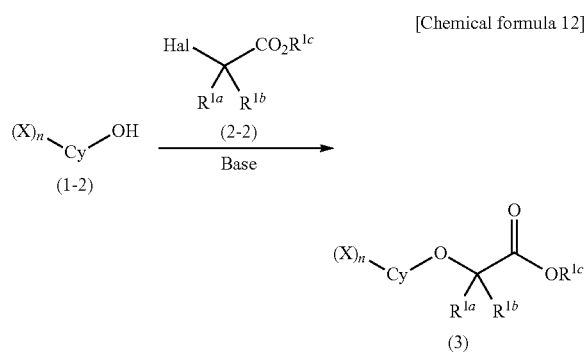

[Chemical formula 12]

a) Compound (3) is obtained by reacting a hydroxyaryl compound represented by formula (1-2) (hereinafter, may be referred to as "compound (1-2)") with an ester compound represented by formula (2-2) (hereinafter, may be referred to as "compound (2-2)") in the presence of a base.

In addition, in formula (1-2) and formula (2-2), X, n, $R^{1a}$, $R^{1b}$ and Cy are as defined above. In formula (2-2), Hal represents a halogen atom, $R^{1c}$ represents a C1-6 alkyl group.

The amount of compound (2-2) is generally 1 to 2 mol, and preferably 1.0 to 1.2 mol with respect to 1 mol of compound (1-2).

Although the reaction may be performed in the absence of a base, it is preferable to perform the reaction in the presence of a base. Examples of the base include pyridine, triethylamine, potassium hydroxide and the like. The amount of the base is generally 1 to 2 mol with respect to 1 mol of compound (1-2).

The reaction may be performed in a solvent. There are no particular limitations on the solvent provided it is inactive against the reaction. Examples of the solvent include ether type solvents such as dioxane, 1,2-dimethoxyethane, tetrahydrofuran; aromatic hydrocarbon type solvents such as toluene, benzene, xylene; aliphatic hydrocarbon type solvents such as n-pentane, n-hexane, n-heptane; halogenated hydrocarbon type solvents such as dichloromethane, chloroform, carbon tetrachloride, 1,2-dichloroethane; amide type solvents such as N,N-dimethyl formamide, N,N-dimethyl acetamide, N-methyl pyrrolidone; nitrile type solvents such as acetonitrile, benzonitrile; and mixed solvents including two or more of these solvents; and the like. Although there are no particular limitations on the amount of the solvent, it is generally 1 to 100 ml with respect to 1 g of compound (1-2).

The reaction temperature ranges from −20° C. to the boiling point of the solvent. Although the reaction time varies according to the reaction scale, it is generally from minutes to hours.

In either reaction described above, after the reaction is completed, an ordinary post-treatment procedure, and if needed, known methods such as distillation, recrystallization or column chromatography, can be carried out to purify and isolate the target compound.

The structure of the target compound can be identified and confirmed by a known analysis such as IR spectroscopy, NMR spectroscopy, mass spectroscopy or elementary analysis.

[Pesticide]

The aryloxyacetamide compound or salt thereof according to the present invention is effective to prevent various pests (including acarus). In particular, it is effective as an acaricide.

[Acaricide]

The following provides an explanation of an acaricide including the compound of the present invention as an active ingredient. Since the compound of the present invention has insecticidal action on adult insects, immature insects, larvae, insect eggs and the like, it can be used to prevent harmful organisms such as acari present on agricultural crops. In particular, the acaricide has a superior prevention effect against acari present on agricultural crops, fruit trees, flowers and ornamental plants, and trees.

Examples of the acari targeted to prevent are shown below.

(1) *Acaridida* of Astigmata order:

(a) Acari belonging to the Acaridae family, for example, *Rhizoglyphus echinopus* and *Rhizoglyphus robini* of *Rhizoglyphus* spp.; *Tyrophagus putrescentiae, Tyrophagus neiswanderi, Tyrophagus perniciosus* and *Tyrophagus similis* of *Tyrophagus* spp.; and others such as *Acarus siro, Aleuroglyphus ovatus, Mycetoglyphus fungivorus;*

(2) *Actinedida* of Prostigmata order (a) Acari belonging to the *Tetranychidae* family, for example, *Bryobia praetiosa* and *Bryobia rubrioculus* of *Bryobia* spp.; for example, *Eotetranychus boreus, otetranychus geniculatus, Eotetranychus pruni, Eotetranychus uncatus, Eotetranychus shii, Eotetranychus suginamensis, Eotetranychus celtis, Eotetranychus smithi, Eotetranychus asiaticus* and *Eotetranychus kankitus* of *Eotetranychus* spp.; for example, *Oligonychus mangiferus, Oligonychus perseae, Oligonychus pustulosus, Oligonychus karamatus, Oligonychus hondoensis, Oligonychus ilicis, Oligonychus ununguis, Oligonychus shinkajii* and *Oligonychus orthius* of *Oligonychus* spp.; for example, *Panonychus citri, Panonychus mori* and *Panonychus ulmi* of *Panonychus* spp.; for example, *Tetranychus viennensis, Tetranychus quercivorus, Tetranychus ludeni, Tetranychus phaselus, Tetranychus cinnabarinus, Tetranychus kanzawai* and *Tetranychus urticae* of *Tetranychus* spp.; *Aponychus corpuzae* and *Aponychus firmianae* of *Aponychus* spp.; *Sasanychus akitanus* and *Sasanychus pusillus* of *Sasanychus* spp.; *Shizotetranychus celarius, Shizotetranychus miscanthi, Shizotetranychus longus, Shizotetranychus schizopus* and *Shizotetranychus recki* of *Shizotetranychus* spp.; and others such as *Tuckerella pavoniformis, Tetranychina harti, Yezonychus sapporensis;*

(b) Acari belonging to the Tenuipalpidae family, for example, *Brevipalpus lewisi*, *Brevipalpus russulus*, *Brevipalpus obovatus* and *Brevipalpus phoenicis* of *Brevipalpus* spp.; for example, *Tenuipalpus pacificus* and *Tenuipalpus zhizhilashviliae* of *Tenuipalpus* spp.; and others such as *Dolichotetranychus floridanus*;

(c) Acari belonging to the Eriophyidae family, for example, *Aceria diospyri*, *Aceria ficus*, *Aceria japonica*, *Aceria kuko*, *Aceria paradianthi*, *Aceria tiyingi*, *Aceria tulipae* and *Aceria zoysiea* of *Aceria* spp.; for example, *Eriophyes chibaensis* and *Eriophyes emarginatae* of *Eriophyes* spp.; for example, *Aculops lycopersici* and *Aculops pelekassi* of *Aculops* spp.; for example, *Aculus fockeui*, *Aculus schlechtendali*, which belong *Aculus* spp.; and others such as *Colomerus vitis*, *Calepitrimerus vitis*, *Phyllocotruta citri*, *Paracalacarus podocarpi*, *Calacarus carinatus*, *Acaphylla theavagrans*, *Paraphytoptus kikus*, *Epitrimerus pyri*;

(d) Acari belonging to the Transonemidae family, for example, *Tarsonemus bilobatus* and *Tarsonemus waitei* of *Tarsonemus* spp.; others such as *Phytonemus pallidus*, *Polyphagotarsonemus latus*;

(e) Acari belonging to the Penthaleidae family, for example, *Penthaleus erythrocephalus* and *Penthaleus major* of *Penthaleus* spp.;

The acaricide including the compound of the present invention has a superior prevention effect against acarus parasitic on animals (prevention of ectoparasite). Examples of the acarus parasitic in animals include those acarus which are parasitic in the back, armpit, underbelly, and inner thigh of host animals to obtain nutritional sources such as blood, dandruff from the animals to live. Examples of the host animals include dogs, cats, mice, rats, hamsters, guinea pigs, squirrels, rabbits, ferrets; pet birds (for example, pigeon, parrot, magpie, java sparrow, parakeet, bengalee, canary); cows, horses, pigs, sheep, goats; poultry (for example, ducks, chickens, quails, geese); bees (for example, *apis mellifera*, Japanese honey bee); and the like.

Examples of the acari targeted to prevent are shown below.

(1) Mite of the Mesostigmata order (a) Acari belonging to the Dermanyssidae family, for example, *Dermanyssus gallinae*;

(b) Acari belonging to the Macronyssidae family, for example, *Ornithonyssus sylviarum*, *Ornithonyssus bursa* and *Ornithonyssus bacoti* of *Ornithonyssus* spp.;

(c) Acari belonging to the Laelapidae family, for example, *Laelaps echidninus* and *Laelaps jettmari* of *Laelaps* spp.; *Tropilaelaps clarae*;

(d) Acari belonging to the Varroidae family, for example, *Varroa destructor*, *Varroa jacobsoni* and *Varroa underwoodi* of *Varroa* spp.;

(2) Tick of the Metastigmata order (a) Acari belonging to the Argasidae family, for example, *Argas persicus* and *Argas reflexus* of *Argas* spp.; for example, *Ornithodoros moubata*, which belongs to *Ornithodoros* spp.;

(b) Acari belonging to the Ixodidae family, for example, *Haemaphysalis concinna*, *Haemaphysalis punctata*, *Haemaphysalis cinnabarina*, *Haemaphysalis otophila*, *Haemaphysalis leachi*, *Haemaphysalis longicornis*, *Haemaphysalis mageshimaensis*, *Haemaphysalis yeni*, *Haemaphysalis campanulata*, *Haemaphysalis pentalagi*, *Haemaphysalis flava*, *Haemaphysalis megaspinosa*, *Haemaphysalis japonica* and *Haemaphysalis douglasi* of *Haemaphysalis* spp.; for example, *Amblyomma americanum*, *Amblyomma variegatum*, *Amblyomma maculatum*, *Amblyomma hebraeum*, *Amblyomma cajennense* and *Amblyomma testudinarium* of *Amblyomma* spp.; for example, *Ixodes ricinus*, *Ixodes hexagonus*, *Ixodes canisuga*, *Ixodes pilosus*, *Ixodes rubicundus*, *Ixodes scapularis*, *Ixodes holocyclus*, *Ixodes ovatus*, *Ixodes persulcatus* and *Ixodes nipponensis* of *Ixodes* spp.; for example, *Rhipicephalus (Boophilus) microplus*), *Rhipicephalus (Boophilus) decoloratus*), *Rhipicephalus (Boophilus) annulatus*), *Rhipicephalus (Boophilus) calceratus*), which belong to *Boophilus* spp.; for example, *Rhipicephalus evertsi*, *Rhipicephalus sanguineus*, *Rhipicephalus bursa*, *Rhipicephalus appendiculatus*, *Rhipicephalus capensis*, *Rhipicephalus turanicus* and *Rhipicephalus zambeziensis* of *Rhipicephalus* spp.; for example, *Dermacentor marginatus*, *Dermacentor reticulatus*, *Dermacentor pictus*, *Dermacentor albipictus*, *Dermacentor andersoni* and *Dermacentor variabilis* of *Dermacentor* spp.;

(3) *Acaridida* of the Astigmata order (a) Acari belonging to the Psoroptidae family, for example, *Psoroptes ovis*, *Psoroptes cuniculi*, *Psoroptes equi*, which are *Psoroptes* spp.; for example, *Chorioptes bovis*, which belongs to *Chorioptes* spp.; *Otodectes cynotis*, which belongs to *Otodectes* spp.;

(b) Acari belonging to the Sarcoptidae family, for example, *Sarcoptes scabiei*, *Sarcoptes canis*, *Sarcoptes bovis*, *Sarcoptes ovis*, *Sarcoptes rupicaprae*, *Sarcoptes equi* and *Sarcoptes suis* of *Sarcoptes* spp.; for example, *Notoedres cati*, which belongs to *Notoedres* spp.;

(c) Acari belonging to the Knemidokoptidae family, for example, *Knemidokoptes mutans*, which belongs to *Knemidokoptes* spp.;

(4) *Actinedida* of the Prostigmata order (a) Acari belonging to the Demodixidae family, for example, *Demodex canis*, *Demodex bovis*, *Demodex ovis*, *Demodex caprae*, *Demodex equi*, *Demodex caballi*, *Demodex suis* and *Demodex cati* of *Demodex* spp.;

(b) Acari belonging to the Trombiculidae family, for example, *Trombicula alfreddugesi* and *Trombicula akamushi* of *Trombicula* spp.;

(c) Acari belonging to the *Tarsonemidae* family, for example, *Acarapis woodi*, which belongs to *Acarapis* spp.;

(Pest Control Agent)

Furthermore, the compound of the present invention may be used to prevent harmful organisms such as pests other than acari present on agricultural crops, sanitary pests, stored grain pests, clothes pests and household pests.

Examples of the pests targeted to prevent are shown below.

(1) Lepidopteran pests, for example, *Spodoptera litura*, *Mamestra brassicae*, *Agrotis ipsilon*, *Autographa nigrisigna*, *Plutella xylostella*, *Adoxophyes honmai*, *Homona magnanima*, *Carposina sasakii*, *Grapholitha molesta*, *Phyllocnistis citrella*, *Caloptilia theivora*, *Phyllonorycter ringoniella*, *Lymantria dispar*, *Euproctis pseudoconspersa*, *Chilo suppressalis*, *Cnaphalocrocis medinalis*, *Ostrinia nubilalis*, *Hyphantria cunea*, *Cadra cautella*, *Heliothis* spp., *Helioverpa*, *Agrotis* spp., *Tinea translucens*, *Cydia pomonella*, *Pectinophora gossypiella*, or the like;

(2) Hemipteran pests, for example, *Myzus persicae*, *Aphis gossypii*, *Lipaphis erysimi*, *Rhopalosiphum padi*, *Riptortus clavatus*, *Acrosternum hilare*, *Unaspis yanonensis*, *Pseudococcus comstocki*, *Trialeurodes vaporariorum*, *Bemisia tabaci*, *Bemisia argentifolii*, *Psylla pyricola*, *Stephanitis nashi*, *Nilaparvata lugens*, *Laodelphax stratella*, *Sogatella furcifera*, *Nephotettix cincticeps*, or the like;

(3) Coleopteran pests, for example, *Phyllotreta striolata*, *Aulacophora indica*, *Leptinotarsa decemlineata*, *Lissorhoptrus oryzophilus*, *Sitophilus oryzae*, *Callosobruchus chinensis*, *Popillia japonica*, *Anomala rufocuprea*, *Diabrotica* spp., *Lasioderma serricorne*, *Lyctus brunneus*, *Monochamus alternatus*, *Anoplophora malasiaca*, *Agriotes* spp., *Epil-*

*achna vigintioctomaculata, Tenebroides mauritanicus, Anthonomus grandis*, or the like;

(4) Dipteran pests, for example, *Bactrocera cucurbitae, Bactrocera dorsalis, Delia platura, Hydrellia griseola, Drosophila melanogaster*, or the like;

(5) Thysanopteran pests, for example, *Thrips palmi, Scirtothrips dorsalis*, or the like;

(6) Hymenopteran pests, for example, *Monomorium pharaonis, Vespa simillima, Athalia rosae*, or the like;

(7) Orthopteran pests, for example, *Locusta migratoria*, or the like;

(8) Blattodea pests, for example, *Blattella germanica, Periplaneta fuligginosa, Periplaneta japonica, Periplaneta americana, Periplaneta australasiae*, or the like;

(9) Isopteran pests, for example, *Coptotermes formosanus, Reticulitermes speratus*, or the like;

(10) Plant parasitic nematodes, for example, *Meloidogyne incognita, Pratylenchus* spp., *Heterodera glycines, Aphelenchoides besseyi, Bursaphelenchus xylophilus*, or the like.

The pesticide including the compound of the present invention has a superior prevention effect against pests parasitic on animals (prevention of ectoparasite).

Examples of the pests targeted to prevent are shown below.
(1) Phthiraptera

Louse belonging to Haematopinidae family, Louse belonging to Linognathidae family, Biting louse belonging to Menoponidae family, Biting louse belonging to Philopteridae family, Biting louse of Trichodectidae family;
(2) Siphonaptera Flea belonging to Pulicidae family, for example, *Ctenocephalides canis* and *Ctenocephalides felis* of *Ctenocephalides* spp.; Flea belonging to Tungidae family, Flea belonging to Ceratophyllidae family, Flea of Leptopsyllidae family;
(3) Pest of Hemiptera;
(4) Pest of Diptera Mosquito belonging to Culicidae family, Black fly belonging to Simuliidae family, Punkie belonging to Ceratopogonidae family, Fly belonging to Tabanidae family, Fly belonging to Muscidae family, *Glossina* belonging to Glossinidae family; Fly belonging to Hippoboscidae family, Fly belonging to Calliphoridae family, Fly belonging to Oestridae family;

The compound of the present invention causes little chemical damage, demonstrates low levels of toxicity in fish and warm-blooded animals, and has a particularly high degree of safety.

The pest control agent of the present invention contains as an active ingredient at least one type of compound selected from the compounds of the present invention.

In addition, although the pest control agent of the present invention may only contain the compound of the present invention, it may also contain carriers such as a solid carrier, liquid carrier or gaseous carrier. In addition, the pest control agent of the present invention may have the compound of the present invention impregnated in a base material such as a porous ceramic plate or non-woven fabric. Moreover, a surfactant or other adjunct may be added as necessary.

The pest control agent according to the present invention can be formulated into a form able to be typically adopted in agricultural chemicals, namely in the form of a water-dispersible powder, granules, powder, emulsion, water-soluble powder, suspension, granular water-dispersible powder, flowable preparation, microcapsules, aerosol, fog, heat transpiration agent, fumigant or poison bait.

Examples of the additives and carriers used when formulating a solid preparation include vegetable powders such as soybean powder or flour, mineral fine powders such as diatomaceous earth, apatite, plaster, talc, bentonite, pyrophillite or clay; and organic and inorganic compounds such as sodium benzoate, urea or sodium sulfate.

Examples of the solvents used when formulating liquid preparations include kerosene, xylene, and petroleum-based aromatic hydrocarbon, cyclohexane, cyclohexanone, dimethylformamide, dimethylsulfoxide, alcohols, acetone, trichloroethylene, methyl isobutyl ketone, mineral oils, vegetable oils and water.

Examples of the gaseous carriers used when formulating propellants include butane gas, LPG, dimethyl ether and carbon dioxide gas.

Examples of the base materials of poison bait include bait components such as grain powder, vegetable oil, sugar or crystalline cellulose, antioxidants such as dimethylhydroxytoluene or nordihydroguaiaretic acid, preservatives such as dehydroacetic acid, accidental swallowing preventives for small children and pets such as cayenne pepper powder, insect-attracting fragrances such as cheese fragrance or onion fragrance.

A surfactant can be added according to need in order to obtain a uniform and stable form during formulation. There are no limitations on the surfactants to be added. Examples of surfactants include nonionic surfactants such as polyoxyethylene alkyl phenyl ethers, polyoxyethylene alkyl ethers, polyoxyethylene higher fatty acid esters, polyoxyethylene sorbitan higher fatty acid esters or polyoxyethylene tristyryl phenyl ethers; sulfate esters of polyoxyethylene alkyl phenyl ethers, alkyl benzene sulfonate, higher fatty alcohol sulfate, alkylnaphthalene sulfonates, polycarboxylates, lignin sulfonates, formaldehyde condensates of alkylnaphthalene sulfonates and isobutylene-maleic anhydride copolymers.

The amount of the compound of the present invention contained in the preparation is preferably 0.01 to 90% by weight, and more preferably 0.05 to 85% by weight.

The water-dispersible powder, emulsion, flowable preparation, water-soluble powder, granular water-dispersible powder which are obtained in this manner can be prepared in the form of a solution, suspension or emulsion and diluted with water to a prescribed concentration to spray onto plants or soil, or in the case of using them in the form of powder or granules, they can be sprayed directly onto plants or soil.

In addition, in the case of using as an acaricide for epidemic prevention, a preparation that is supplied in the form of oil solution, aerosol, fog, poison bait or miticidal sheet can be directly used.

In addition, in the case of using the pest control agent of the present invention to prevent animal parasitic acari of livestock such as cows or pigs and pets such as dogs or cats, the compound of the present invention can be used at a ratio of 0.01 mg to 1000 mg per 1 kg of host animal.

An acaricide for preventing acari can be applied using a known veterinary method. Examples of such methods include methods in which the acaricide is administered to an animal by a tablet, capsule, immersion liquid, food additive, suppository or injection (intramuscular, subcutaneous, intravenous or intraabdominal injection) when administered for the purpose of systemic control, methods in which an oily or aqueous liquid preparation is administered by spraying, pouring on or spotting on when administered for the purpose of non-systemic control, and methods in which the acaricide is mixed with a resin and the kneaded product is molded into a suitable shape such as that of a collar or ear tag which is then attached to the animal.

The pest control agent of the present invention can be mixed or combined with fungicides, other insecticides or acaricides, nematocides, soil pesticides, plant regulators, synergists, fertilizers, soil improvers or animal feeds and the like.

The following lists typical examples of fungicides, other insecticides or acaricides, nematocides, soil pesticides and plant regulators able to be used by mixing with the pest control agent of the present invention.

Insecticides, acaricides, nematocides, soil pesticides and antiparasitic agent:

(1) organic (thio)phosphate-based: such as acephate, azamethiphos, azinphos-methyl, azinphos-ethyl, bromophos-ethyl, bromfenvinphos, BRP, chlorpyriphos, chlorpyriphos-methyl, chlorpyrifos-ethyl, chlorfenvinphos, cadusafos, carbophenothion, chlorethoxyfos, chlormephos, coumaphos, cyanofenphos, cyanophos, CYAP, diazinon, dichlorvos, dicrotophos, dimethoate, disulfoton, demeton-S-methyl, dimethylvinfos, demeton-S-methyl sulphone, dialifos, diazinon, dichlofenthion, dioxabenzofos, disulfoton, ethion, ethoprophos, etrimfos, EPN, fenamiphos, fenitrothion, fenthion, fensulfothion, flupyrazofos, fonofos, formothion, fosmethilan, heptenophos, isazophos, iodofenphos, isofenphos, isoxathion, iprobenfos, malathion, mevinphos, methamidophos, methidathion, monocrotophos, mecarbam, methacrifos, naled, omethoate, oxydemeton-metyl, paraoxon, parathion, parathion-methyl, phenthoate, phosalone, phosmet, phosphamidon, phorate, phoxim, pirimiphos-methyl, pirimiphos-ethyl, profenofos, prothiofos, fosthiazete, phosphocarb, propaphos, propetamphos, prothoate, pyridafenthion, pyraclofos, quinalphos, salithion, sulprofos, sulfotep, tetrachlorvinphos, terbufos, triazophos, trichlorfon, tebupirimfos, temephos, thiomethon, vamidothion, pyraclofos;

(2) carbamate-based: alanycarb, aldicarb, bendiocarb, benfuracarb, carbaryl, carbofuran, carbosulfan, fenoxycarb, fenothiocarb, methiocarb, methomyl, oxamyl, pirimicarb, propoxur, thiodicarb, triazamate, ethiofencarb, fenobucarb, MIPC, MPMC, MTMC, pyridafenthion, furathiocarb, XMC, aldoxycarb, allyxycarb, aminocarb, bufencarb, butacarb, butocarboxim, butoxycarboxim, cloethocarb, dimetilan, formetanate, isoprocarb, metam-sodium, metolcarb, thiofanox, trimethacarb, xylycarb;

(3) pyrethroid-based: allethrin, bifenthrin, cyfluthrin, β-cyfluthrin, cyhalothrin, lambdacyhalothrin, cyphenothrin, cypermethrin, alphacypermethrin, betacypermethrin, zeta-cypermethrin, deltamethrin, esfenvalerate, etofenprox, fenpropathrin, fenvalerate, imiprothrin, permethrin, prallethrin, pyrethrin, pyrethrin I, pyrethrin II, resmethrin, silafluofen, fluvalinate, tefluthrin, tetramethrin, tralomethrin, transfluthrin, profluthrin, dimefluthrin, acrinathrin, cycloprothrin, halfenprox, flucythrinate, bioallethrin, bioethanomethrin, biopermethrin, bioresmethrin, transpermethirn, empenthrin, fenfluthrin, fenpirithrin, flubrocythrinate, lufenoprox, flumethrin, metofluthrin, phenothrin, protrifenbute, pyresmethrin, terallethrin;

(4) growth regulators:
(a) chitin synthesis inhibitors: chlorfluazuron, diflubenzuron, flucycloxuron, flufenoxuron, hexaflumuron, lufenuron, novaluron, teflubenzuron, triflumuron, bistrifluron, nobifumuron, buprofezin, hexythiazox, etoxazole, clofentezine, fluazuron, penfluron;
(b) ecdysone antagonists: halofenozide, methoxyfenozide, tebufenozide, chromafenozide, azadirachtin;
(c) juvenile hormone-like substances: pyriproxyfen, methoprene, diofenolan, epofeneonane, hydroprene, kinoprene, triprene;
(d) lipid biosynthesis inhibitors: spirodiclofen, spiromesifen, spirotetramat, flonicamid;
(5) nicotine receptor agonist/antagonist compounds: acetamiprid, clothianidine, dinotefuran, imidacloprid, nitenpyram, thiacloprid, thiamethoxam, nithiazine, nicotine, bensultap, cartap; flupyradifurone;

(6) GABA antagonist compounds:
(a) acetochlor, ethiprole, fipronil, vaniliprole, pyrafluprole, pyriprole;
(b) organochlorine compound: camphechlore, chlordane, endosulfan, HCH, γ-HCH, heptachlor, methoxychlor;
(7) macrocyclic lactone insecticides: abamectin, emamectin, milbemectin, lepimectin, spinosad, ivermectin, seramectin, doramectin, epinomectin, moxidectin; milbemycin; milbemycin oxime;
(8) METI I compounds: fenazaquin, pyridaben, tebufenpyrad, tolfenpyrad, flufenirim, hydramethylnon, fenpyroximate, pyrimidifen, dicofol;
9) METI II and III compounds: acequinocyl, fluacrypyrim, rotenone;
(10) uncoupling agent compounds: chlorfenapyr, dinobuton, dinocap, DNOC;
11) oxidative phosphorylation inhibitor compounds: cyhexitin, diafenthiuron, fenbutatin oxide, propargite, azocyclotin;
(12) molting disruption compounds: cyromazine;
(13) mixed function oxidase inhibitor compounds: piperonyl butoxide;
(14) sodium channel blocker compounds: indoxacarb, metaflumizone;
(15) microbial pesticides: BT agents, insect pathogen viral agents, insect pathogen fungal agents, nematode pathogen fungal agents, *bacillus, beauveria bassiana, metarhizium anisopliae, paecilomyces, thuringiensin, verticillium;*
(16) latrophilin receptor agonist: depsipeptide, cyclodepsipeptide, 24-membered cyclodepsipeptide, emodepside;
(17) octopamine agonist: amitraz;
(18) ryanodine derivative agonist: flubendiamide, chlorantraniliprole, cyantraniliprole;
(19) magnesium-stimulated ATPase inhibitor: thiocyclarm, thiosultap, nereistoxin;
(20) antifeedant: pymetrozine;
(21) acari growth inhibitor: clofentezine, etoxazole;
(22) other compounds: benclothiaz, bifenazate, pyradalyl, sulfur, cyenopyrafen, cyflumetofen, amidoflumet, tetradifon, chlordimeform, 1,3-dichloropropene, DCIP, phenisobromolate, benzomate, methaldehyde, spinetoram, pyrifluquinzaon, benzomate, bromopropylate, quinomethionate, chlorobenzilate, chloropicrin, chlothiazoben, dicyclanil, fenoxacrim, fentrifanil, flubenzimine, fluphenazine, gossyplure, japonilure, metoxadiazone, oil, potassium oleate, sulfluramid, tetrasul, triarathene; afidopyropen, pyflubumide, flometoquin, flufiprole, fluensulfone, meperfluthrin, tetramethylfluthrin, sulfoxaflor, imicyafos, tralopyril, diflovidazin, dimefluthrin, methylneodecanamide;
(23) antiparastic agent
(a) benzimidazoles: fenbendazole, albendazole, triclabendazole, oxibendazole;
(b) salicylanilides: closantel, oxyclozanide;
(c) substituted phenols: nitroxinil;
(d) pyridines: pyrantel;
(e) imidazothiazoles: levamisole;
(f) tetrahydropyrimidines: praziquantel;
(g) other antiparastic agents: cyclodien, riania, clorsulon, metronidazole, demijitorazu;

Fungicides:
(1) benzimidazole-based: benomyl, carbendazim, fuberidazole, thiabendazole, methyl thiophanate; chlorfenazole;
(2) dicarboxyimide-based fungicides: chlozolinate, iprodione, procymidone, vinclozolin;
(3) DMI fungicides: imazalil, oxpoconazole, pefurazoate, prochloraz, triflumizole, triforine, pyrifenox, fenarimol, nuarimol, azaconazole, bitertanol, bromconazole, cyproconazole, difenoconazole, diniconazole, epoxyconazole, fenbuconazole, fluquinconazole, flusilazole, flutriafol, hexaconazole, imibenconazole, ipuconazole, metconazole, myclobutanil, penconazole, propiconazole, prothioconazole, simeconazole, tebuconazole, tetraconazole, triadimefon, triadimenol, triticonazole, etaconazole, furconazole-cis; diclobutrazol, diniconazole-M, dodemorph-acetate, furconazole, imazalil-sulphate, nafuchifen, uniconazole P, viniconazole, voriconazole;

(4) phenylamide-based: benalaxyl, furalaxyl, metalaxyl, metalaxyl-M, oxadixyl, ofurace; benalaxyl-M, clozylacon;

(5) amine-based: aldimorph, dodemorph, fenpropimorph, tridemorph, fenpropidine, piperalin, spiroxamine;

(6) phosphothiolate-based: EDDP, iprobenfos, pyrazophos;

(7) dithiolane-based: isoprothiolane;

(8) carboxamide-based: benodanil, boscalid, carboxin, fenfuran, flutolanil, furametpyr, mepronil, oxycarboxin, penthiopyrad, thifluzamide; bixafen, isopyrazam, penflufen, fluxapyroxad, Sedaxan;

(9) hydroxy(2-amino)pyrimidine-based: bupirimate, dimethirimol, ethirimol;

(10) AP fungicides (anilinopyrimidines-based): cyprodinil, mepanipyrim, pyrimethanil or the like; andoprim;

(11) N-phenylcarbamate-based: diethofencarb;

(12) QoI fungicides (Qo inhibitor-based): azoxystrobin, picoxystrobin, pyraclostrobin, kresoxim-methyl, trifloxystrobin, dimoxystrobin, metominostrobin, orysastrobin, famoxadone, fluoxastrobin, fenamidone, metominofen; ametoctradin, pyrametostrobin, pyraoxystrobin, pyribencarb; coumethoxystrobin, coumoxystrobin, enestroburin, fenoxystrobin, triclopyricarb;

(13) PP fungicides (phenylpyrrole-based): fenpiconil, fludioxonil;

(14) quinoline-based: quinoxyfen;

(15) AH fungicides (aromatic hydrocarbon-based): biphenyl, chloroneb, dichloran, quintozene, tecnazene;

(16) MBI-R-based: fthalide, pyroquilon, tricyclazole;

(17) MBI-D-based: carpropamid, diclocymet, fenoxanil;

(18) SBI agents: fenhexamid, pyributicarb, terbinafine;

(19) phenylureas: pencycuron;

(20) Qil fungicides (Qi inhibitors): cyazofamid; amisulbrom, furmecyclox;

(21) benzamide-based: zoxamide;

(22) enopyranurone-based: blasticidin;

(23) hexopyranosyl-based: kasugamycin; kasugamycin hydrochloride;

(24) glucopyranosyl-based: streptomycin, validamycin; validamycin A;

(25) cyanoacetoamide-based: cymoxanil;

(26) carbamate-based: iodocarb, propamocarb, prothiocarb, polycarbamate;

(27) uncoupling agents: binapacryl, dinocap, ferimzone, fluazinam; meptyldinocap;

(28) organic tin compounds: triphenyltin acetate, triphenyltin chloride, triphenyltin hydroxide;

(29) phosphate esters: phosphonic acid, tolclofos-methyl, fosetyl; tolctophos-methyl;

(30) phthalamide-based: tecloftalam;

(31) benzotriazine-based: triazoxide;

(32) benzene sulfonamide-based: flusulfamide;

(33) pyridazinones: diclomezine;

(34) CAA fungicide (carboxylic amide)-based: dimethomorph, flumorph, benthiavalicarb-isopropyl, iprovalicarb, mandipropamide; valifenalate;

(35) tetracyclines: oxytetracycline;

(36) thiocarbamate-based: methasulfocarb;

(37) other compounds: etridiazole, polyoxins, oxolinic acid, hydroxyisoxazole, octinoline, silthiofam, diflumetorim, acibenzolar-s-methyl, probenazole, tiadinil, ethaboxam, cyflufenamid, proquinazid, metrafenone, fluopicolide, cupric hydroxide, organic copper, sulfur, ferbam, manzeb, maneb, metiram, propineb, thiuram, zineb, ziram, captan, captafol, folpet, chlorothalonil, dichlofluanid, tolylfluanid, dodine, guazatine, iminoctadine acetate, iminoctadine dodecylbenzene sulfonate, anilazine, dithianon, chloropicrin, dazomet, chinomethionat, cyprofuram, silthiofam, *agrobacterium*, fluoroimide. isotianil, polyoxorim, bordeaux mixture, copper naphthalate, copper oxide, oxychloride copper, sulfuric acid copper, copper man, bis(8-quinolinolato) copper(II), calcium polysulfide, iminoctadine; isofetamido, tolprocarb, fenpyrazamine, pyriofenone, tebufloquin, flupyram, zarilamide; fluor folpet, propamidine, edifenphos; benthiazole, bethoxazin, capsaicin, carvone, curfraneb, mancozeb, cyprosulfamide, debacarb, dichlorophen, difenzoquat, difenzoquat methyl sulfonate, diphenylamine, flumetover, fluoroimide, flutianil, fosetyl-aluminum, fosetyl-calcium, fosetyl-sodium, irmamycin, methylisothiocyanate (MITC), mildew-mycin, natamycin, nitrothal isopropyl, oxamocarb, oxyphenthiin, propamocarb-fosetylate, puropamocin sodium, pyrimorph, pyrrolnitrin, tolnifanide, trichlaamide;

Examples of the plant growth regulators include:

abscisic acid, indole butyric acid, uniconazole, ethychlozate, ethephon, cloxyfonac, chlormequat, chlorella extract, calcium peroxide, cyanamide, dichlorprop, gibberellin, daminozide, decyl alcohol, trinexapac-ethyl, mepiquat-chloride, paclobutrazol, paraffin wax, piperonyl butoxide, pyraflufen ethyl, flurprimidol, prohydrojasmon, prohexadione-calcium, benzylaminopurine, pendimethalin, forchlorfenuron, potassium hydrazide maleate, 1-naphthylacetoamide, 4-CPA, MCPB, choline, oxyquinoline sulfate, ethychlozate, butralin, 1-methylcyclopropene, aviglycine hydrochloride.

EXAMPLES

The following provides Examples to explain the present invention more specifically. However, the present invention is not limited to the following examples.

Example 1

Production of 2-(4-bromo-3,5-dichlorophenoxy)-N-[2-(pyridine-2-yl)propan-2-yl]butyramide Step 1

Production of Compound 1 (ethyl 2-(4-bromo-3,5-dichlorophenoxy)butanoate)

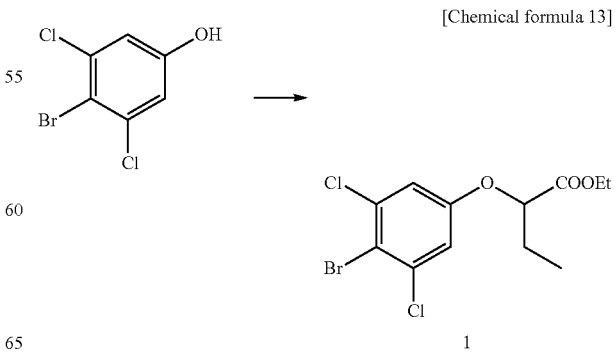

[Chemical formula 13]

2.00 g of 4-bromo-3,5-dichlorophenol was dissolved in 40 ml of N,N-dimethyl formamide. 0.36 g of sodium hydride was added to the resulting solution, followed by stirring for 1 hour at room temperature. 1.94 g of 2-bromobutyric acid ethyl was then added to the resulting mixture, followed by stirring for 3 hours at 60° C. Then, brine was added to the resulting mixture, followed by extracting with ethyl acetate. The resulting organic layer was dried by adding magnesium sulfate and filtered, followed by distilling the solvent under reduced pressure. The resulting residue was purified by silica gel column chromatography to obtain 2.91 g of compound 1 (yield: 99%). The NMR analysis result of compound 1 is shown below.

$^1$H-NMR (CDCl$_3$/TMS, δ(ppm)) 6.92(s, 2H), 4.49(dd, 1H), 4.23(q, 2H), 2.03-1.95(m, 2H), 1.26(t, 3H), 1.05(t, 3H)

Step 2

Production of Compound 2
(2-(4-bromo-3,5-dichlorophenoxy)butanoic acid)

[Chemical formula 14]

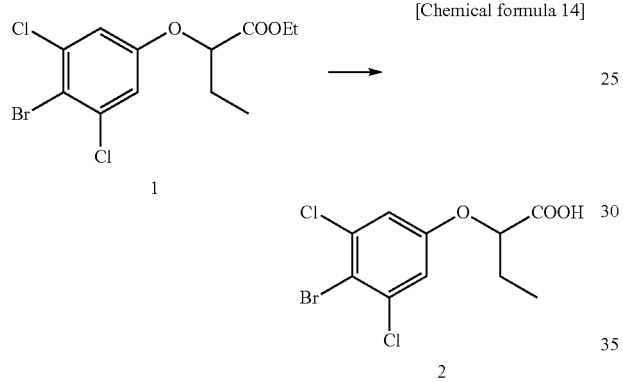

2.91 g of compound 1 was dissolved in 40 ml of tetrahydrofuran and 10 ml of water. 0.49 g of sodium hydride was added to the resulting solution, followed by stirring for 3 hours at 60° C. 1% hydrochloric acid was then added to the resulting solution to adjust the pH to 4, followed by extracting with ethyl acetate. The resulting organic layer was dried by adding magnesium sulfate and filtered. The solvent was then distilled under reduced pressure to obtain 2.52 g of the target compound 2 (yield: 94%). The NMR analysis result of compound 2 is shown below.

$^1$H-NMR (CDCl$_3$/TMS, δ(ppm)) 6.95(s, 2H), 4.58(dd, 1H), 2.05-2.00(m, 2H), 1.09(t, 3H)

Step 3

Production of Compound 3 (2-(4-bromo-3,5-dichlorophenoxy)-N-[2-(pyridine-2-yl)propan-2-yl]butyramide)

[Chemical formula 15]

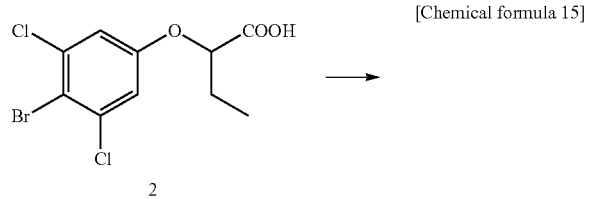

0.40 g of compound 2 was dissolved in 20 ml of acetonitrile. 0.21 g of 2-(pyridine-2-yl)propane-2-amine, 0.33 g of 1-ethyl-3-(3-dimethyl aminopropyl)carbodiimide hydrochloride, 0.18 g of 1-hydroxybenzotriazole and 0.25 g of triethylamine were added to the resulting solution, followed by stirring overnight at room temperature. Water was then added to the resulting mixture, followed by extracting with ethyl acetate. The resulting organic layer was dried by adding magnesium sulfate and filtered, followed by distilling the solvent under reduced pressure. The resulting residue was purified by silica gel column chromatography to obtain 0.14 g of compound 3 (yield: 26%).

Example 2

Production of 2-[2-bromo-6-(trifluoromethyl)pyridin-4-yloxy]-N-8 2-(pyridin-2-yl)propan-2-yl]butyramide Step 1

Production of Compound 4 (ethyl 2-[2-bromo-6-(trifluoromethyl)pyridin-4-yloxy]butanoate)

[Chemical formula 16]

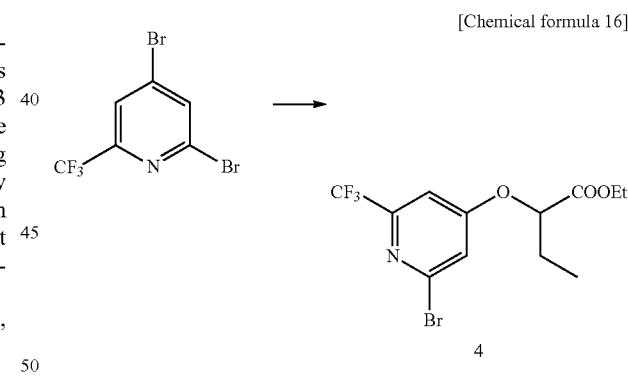

0.75 g of 2,4-dibromo-6-(trifluoromethyl)pyridine and 0.37 g of 2-hydroxybutyric acid ethyl were dissolved in 15 ml of N,N-dimethyl formamide. 0.12 g of 55% sodium hydride was added to the resulting solution followed by stirring for 1 hour at room temperature while cooling with ice. Ammonium chloride aqueous solution was then added to the resulting solution, followed by extracting with ethyl acetate. The resulting organic layer was dried by adding magnesium sulfate and filtered, followed by distilling the solvent under reduced pressure. The resulting residue was purified by silica gel column chromatography to obtain 0.43 g of compound 4 (yield: 49%). The NMR analysis result of compound 4 is shown below.

$^1$H-NMR (CDCl$_3$/TMS, δ(ppm)) 7.15(d, 1H), 7.07(d, 1H), 4.67(dd, 1H), 4.31-4.23(m, 2H), 2.09-2.01(m, 2H), 1.28(t, 3H), 1.08(t, 3H)

Step 2

Production of compound 5 (2-[2-bromo-6-(trifluoromethyl)pyridin-4-yloxy]butanoic acid)

[Chemical formula 17]

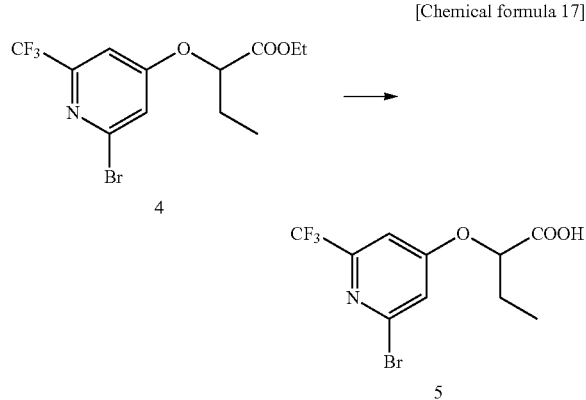

0.43 g of compound 4 was dissolved in 12 ml of tetrahydrofuran, 3 ml of methanol and 3 ml of water. 0.10 g of lithium hydroxide monohydrate was added to the resulting solution followed by stirring overnight at room temperature. 1% hydrochloric acid was then added to the resulting solution to adjust the pH to 4, followed by extracting with ethyl acetate. The resulting organic layer was dried by adding magnesium sulfate and filtered, followed by distilling the solvent under reduced pressure to obtain 0.38 g of compound 5 (yield: 95%). The NMR analysis result of compound 5 is shown below.

$^1$H-NMR (CDCl$_3$/TMS, δ(ppm)) 9.34(br, 1H), 7.17(d, 1H), 7.09(d, 1H), 4.76(dd, 1H), 2.19-2.03(m, 2H), 1.12(t, 3H)

Step 3

Production of Compound 6 (2-[2-bromo-6-(trifluoromethyl)pyridin-4-yloxy]-N-[2-(pyridin-2-yl)propan-2-yl]butyramide)

[Chemical formula 18]

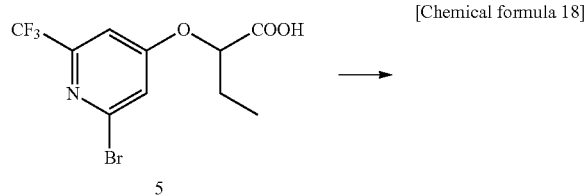

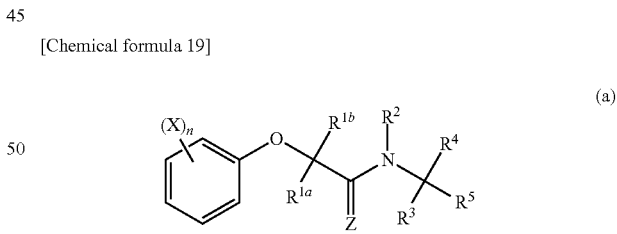

0.18 g of compound 5 was dissolved in 15 ml of acetonitrile. 0.11 g of 2-(pyridine-2-yl)propane-2-amine, 0.15 g of 1-ethyl-3-(3-dimethyl aminopropyl)carbodiimide hydrochloride, 0.08 g of 1-hydroxybenzotriazole, and 0.11 g of triethylamine were added to the resulting solution, followed by stirring overnight at room temperature. Water was then added to the resulting solution, followed by extracting with ethyl acetate. The resulting organic layer was dried by adding magnesium sulfate and filtered, followed by distilling the solvent under reduced pressure. The resulting residue was purified by silica gel column chromatography to obtain 0.16 g of compound 6 (yield: 67%) having a melting point of 123 to 125° C.

Examples of the aryloxyacetamide compound of the present invention which can be produced by the methods described above are shown in TABLES 1 to 3. TABLE 1 shows the substituents of the compound represented by formula (a). TABLE 2 shows the substituents of the compound represented by formula (b). TABLE 3 shows the substituents of the compound represented by formula (c). In addition, TABLES 1 to 3 show only a part of aryloxyacetamide compounds of the present invention. An ordinary skilled person can easily understand that other compounds which are not shown in this description, namely, the compounds which are substituted by various substituents complying with the purpose and scope of the present invention can also be obtained by the above-described method and can be used.

[Chemical formula 19]

(a)

$$\text{(X)}_n\text{-Ar-O-C(R}^{1a}\text{)(R}^{1b}\text{)-C(=Z)-N(R}^2\text{)-C(R}^3\text{)(R}^4\text{)-R}^5$$

TABLE 1

| No. | $R^{1a}$ | $R^{1b}$ | $R^2$ | $R^3$ | $R^4$ | $R^5$ | (X)n | Z | Melting Point ° C. |
|---|---|---|---|---|---|---|---|---|---|
| 1-1 | Et | H | H | Me | Me | Py-2-yl | 3,5-Cl$_2$ | O | 108-110 |
| 1-2 | Et | H | H | Me | Me | Py-2-yl | 3-CH$_2$CH$_2$O-4 | O | 58-60 |
| 1-3 | Et | H | H | Me | Me | Py-2-yl | 3,5-Me$_2$ | O | 90-92 |
| 1-4 | Et | H | H | Me | Me | Py-2-yl | 4-Br$_3$,5-Cl$_2$ | O | * |
| 1-5 | Et | H | H | Me | Me | Py-2-yl | 3,4-Cl$_2$ | O | 78-80 |
| 1-6 | OMe | H | H | Me | Me | Py-2-yl | 3,5-Cl$_2$ | O | 55-57 |
| 1-7 | Et | H | H | Me | Me | Pyrimidin-2-yl | 4-Br$_3$,5-Cl$_2$ | O | 109-111 |
| 1-8 | $^n$Pr | H | H | Me | Me | Py-2-yl | 3,5-Cl$_2$ | O | 96-98 |

TABLE 1-continued

| No. | $R^{1a}$ | $R^{1b}$ | $R^2$ | $R^3$ | $R^4$ | $R^5$ | (X)n | Z | Melting Point °C. |
|---|---|---|---|---|---|---|---|---|---|
| 1-9 | SMe | H | H | Me | Me | Py-2-yl | 3,5-Cl$_2$ | O | 133-135 |
| 1-10 | SMe | H | H | Me | Me | 4-Ph—Py-2-yl | 3,5-Cl$_2$ | O | 129-131 |
| 1-11 | Me | H | H | Me | Me | Py-2-yl | 3,5-Cl$_2$ | O | 109-111 |
| 1-12 | Ph | H | H | Me | Me | Py-2-yl | 3,5-Cl$_2$ | O | 153-155 |
| 1-13 | Et | H | H | Me | Me | Py-2-yl | 3,5-Br$_2$-4-Cl | O | 131-133 |
| 1-14 | Et | H | H | Me | Me | Pyrimidin-2-yl | 3,5-Br$_2$-4-Cl | O | 121-123 |
| 1-15 | Et | H | H | Me | Me | Py-2-yl | 2,4-Cl$_2$ | O | 76-78 |
| 1-16 | Et | H | H | Me | Me | Py-2-yl | 3,4-Br$_2$-5-Cl | O | * |
| 1-17 | Et | H | H | Me | Me | 4-Ph—Py-2-yl | 3,4-Br$_2$-5-Cl | O | * |
| 1-18 | Et | H | H | Me | Me | Pyrimidin-2-yl | 3,4-Br$_2$-5-Cl | O | 144-145 |
| 1-19 | Me | Me | H | Me | Me | Py-2-yl | 3,5-Cl$_2$ | O | 79-81 |
| 1-20 | Et | H | H | Me | Me | Py-2-yl | 2,6-Cl$_2$ | O | * |
| 1-21 | —(CH$_2$)$_5$— | | H | Me | Me | Py-2-yl | 3,5-Cl$_2$ | O | 117-119 |
| 1-22 | —(CH$_2$)$_4$— | | H | Me | Me | Py-2-yl | 3,5-Cl$_2$ | O | 113-115 |

TABLE 2

| No. | $R^{1a}$ | $R^{1b}$ | $R^2$ | $R^3$ | $R^4$ | $R^5$ | (X)n | Z | Melting Point °C. |
|---|---|---|---|---|---|---|---|---|---|
| 1-23 | Et | H | H | Me | Me | 4-Ph—Py-2-yl | 4-Br$_3$,5-Cl$_2$ | O | * |
| 1-24 | Et | H | H | Me | Me | Py-2-yl | 3,5-Cl$_2$ | O | * |
| 1-25 | Et | H | H | Me | Me | Py-2-yl | 3-Br$_5$—Cl | O | 110-112 |
| 1-26 | Et | H | H | Me | Me | Py-2-yl | 4-OMe-3,5-Br$_2$ | O | 79-81 |
| 1-27 | Et | H | H | Me | Me | 4-SMe-Py-2-yl | 4-Br$_3$,5-Cl$_2$ | O | 134-136 |
| 1-28 | Et | H | H | Me | Me | Py-2-yl | 3,4,5-Br$_3$ | O | 124-126 |
| 1-29 | Et | H | H | Me | Me | 4-SO$_2$Me-Py-2-yl | 4-Cl-3,5-Br$_2$ | O | 136-138 |
| 1-30 | Et | H | H | Me | Me | 5-F-Py-2-yl | 4-Cl-3,5-Br$_2$ | O | 112-114 |
| 1-31 | Et | H | H | Me | Me | Py-2-yl | 3,4,5-Cl$_3$ | O | 89-91 |
| 1-32 | Et | H | H | Me | Me | 4-$^t$Bu-Py-2-yl | 4-Cl-3,5-Br$_2$ | O | 44-46 |
| 1-33 | H | H | H | Me | Me | Py-2-yl | 3,5-Cl$_2$ | O | 96-98 |
| 1-34 | Et | H | H | Me | Me | Pyrimidin-2-yl | 4-Cl-3,5-Br$_2$ | S | * |
| 1-35 | OPh | H | H | Me | Me | Py-2-yl | 3,5-Cl$_2$ | O | * |
| 1-36 | $^c$Hex | H | H | Me | Me | Py-2-yl | 3,5-Cl$_2$ | O | 155-157 |
| 1-37 | Et | H | H | Me | Me | 5-SMe-Py-2-yl | 4-Cl-3,5-Br$_2$ | O | 128-130 |
| 1-38 | Et | H | H | Me | Me | 5-SO$_2$Me-Py-2-yl | 4-Cl-3,5-Br$_2$ | O | 162-164 |
| 1-39 | Et | H | H | Me | Me | Py-2-yl | 3-Cl-5-CF$_3$ | O | 106-108 |
| 1-40 | Et | H | H | Me | Me | Pyrimidin-2-yl | 3-Cl-5-CF$_3$ | O | 81-83 |
| 1-41 | Et | H | H | Me | Me | Py-2-yl | 3-Cl-5-CN | O | 90-92 |
| 1-42 | Et | H | H | Me | Me | Py-2-yl | 3,5-Br$_2$ | O | 123-125 |
| 1-43 | Et | H | H | Me | Me | Pyrimidin-2-yl | 3-Cl-5-CN | O | 86-88 |
| 1-44 | CH$_3$—CH= | H | H | Me | Me | Py-2-yl | 3,5-Cl$_2$ | O | 110-112 |
| 1-45 | CH$_3$—CH= | H | H | Me | Me | 4-SMe-Py-2-yl | 3,5-Cl$_2$ | O | * |
| 1-46 | CH$_3$—CH= | H | H | Me | Me | 4-SO$_2$Me-Py-2-yl | 3,5-Cl$_2$ | O | 96-98 |
| 1-47 | Et | H | H | Me | Me | 4-SMe-Py-2-yl | 3-Cl-5-CN | O | 108-110 |
| 1-48 | Et | H | H | Me | Me | 4-SO$_2$Me-Py-2-yl | 3-Cl-5-CN | O | 161-163 |

[Chemical formula 20]

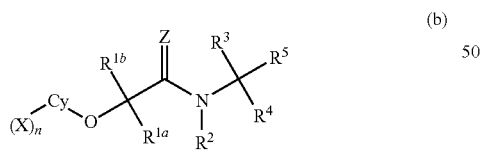

(b)

TABLE 3

| No. | $R^{1a}$ | $R^{1b}$ | $R^2$ | $R^3$ | $R^4$ | $R^5$ | Cy | (X)n | Z | Melting Point °C. |
|---|---|---|---|---|---|---|---|---|---|---|
| 2-1 | Et | H | H | Me | Me | Py-2-yl | Quinolin-6-yl | — | O | 111-113 |
| 2-2 | Et | H | H | Me | Me | Py-2-yl | Benzothiazol-6-yl | — | O | 102-104 |
| 2-3 | Et | H | H | Me | Me | Pyrimidin-2-yl | Benzothiazol-6-yl | — | O | 145-147 |
| 2-4 | OMe | H | H | Me | Me | Py-2-yl | Benzothiazol-6-yl | — | O | * |
| 2-5 | Et | H | H | Me | Me | Py-2-yl | Py-2-yl | 6-CF$_3$ | O | * |
| 2-6 | SMe | H | H | Me | Me | Py-2-yl | Benzothiazol-6-yl | — | O | 91-93 |
| 2-7 | SMe | H | H | Me | Me | 4-Ph—Py-2-yl | Benzothiazol-6-yl | — | O | 153-155 |

TABLE 3-continued

| No. | $R^{1a}$ | $R^{1b}$ | $R^2$ | $R^3$ | $R^4$ | $R^5$ | Cy | $(X)n$ | Z | Melting Point °C. |
|---|---|---|---|---|---|---|---|---|---|---|
| 2-8 | Et | H | H | Me | Me | Pyrimidin-2-yl | Py-4-yl | 2-Br$_6$—CF$_3$ | O | 114-116 |
| 2-9 | Et | H | H | Me | Me | Py-2-yl | Py-4-yl | 2-Br$_6$—CF$_3$ | O | 123-125 |
| 2-10 | Et | H | H | Me | Me | Py-2-yl | Py-4-yl | 2,6-Cl$_2$ | O | 110-111 |
| 2-11 | Et | H | H | Me | Me | 4-Ph—Py-2-yl | Py-4-yl | 2,6-Cl$_2$ | O | * |
| 2-12 | Et | H | H | Me | Me | Pyrimidin-2-yl | Py-4-yl | 2,6-Cl$_2$ | O | 132-133 |
| 2-13 | Et | H | H | Me | Me | Py-2-yl | Py-2-yl | 4-CF$_3$-6-Cl | O | 116-117 |
| 2-14 | Et | H | H | Me | Me | 4-Ph—Py-2-yl | Py-2-yl | 4-CF$_3$-6-Cl | O | 114-115 |
| 2-15 | Et | H | H | Me | Me | Pyrimidin-2-yl | Py-2-yl | 4-CF$_3$-6-Cl | O | 80-81 |
| 2-16 | Et | H | H | Me | Me | Py-2-yl | Py-4-yl | 2-Cl-6-N(Me)$_2$ | O | 123-124 |

TABLE 4

| No. | $R^{1a}$ | $R^{1b}$ | $R^2$ | $R^3$ | $R^4$ | $R^5$ | Cy | $(X)n$ | Z | Melting Point °C. |
|---|---|---|---|---|---|---|---|---|---|---|
| 2-17 | Me | Me | H | Me | Me | Py-2-yl | Py-2-yl | 5-Cl | O | * |
| 2-18 | Et | Et | H | Me | Me | Py-2-yl | Py-4-yl | 2,6-Cl$_2$ | O | 136-138 |
| 2-19 | Me | Me | H | Me | Me | Py-2-yl | Py-2-yl | 3-Cl-5-CF$_3$ | O | * |
| 2-20 | Et | Me | H | Me | Me | Py-2-yl | Py-4-yl | 2,6-Cl$_2$ | O | 87-89 |
| 2-21 | Et | Me | H | Me | Me | Pyrimidin-2-yl | Py-4-yl | 2,6-Cl$_2$ | O | * |
| 2-22 | Et | H | H | Me | Me | Py-2-yl | Py-4-yl | 2,6-Br$_2$ | O | 134-135 |
| 2-23 | Et | H | H | Me | Me | Pyrimidin-2-yl | Py-4-yl | 2,6-Br$_2$ | O | 139-140 |
| 2-24 | Et | H | H | Me | Me | 4-SMe-Py-2-yl | Py-4-yl | 2,6-Cl$_2$ | O | * |
| 2-25 | Et | H | H | Me | Me | 4-SO$_2$Me-Py-2-yl | Py-4-yl | 2,6-Cl$_2$ | O | 179-181 |
| 2-26 | Et | H | H | Me | Me | Py-2-yl | Pyrimidin-4-yl | 2-Me-6-Cl | O | 119-121 |
| 2-27 | Et | H | H | Me | Me | Py-2-yl | Pyrimidin-2-yl | 4,6-Me$_2$ | O | 65-67 |
| 2-28 | Et | H | H | Me | Me | 4-SOMe-Py-2-yl | Py-4-yl | 2,6-Cl$_2$ | O | 200-202 |
| 2-29 | Et | H | H | Me | Me | 4-SMe-Py-2-yl | Py-4-yl | 4-CF$_3$-6-Cl | O | 116-118 |
| 2-30 | Et | H | H | Me | Me | 4-SO$_2$Me-Py-2-yl | Py-2-yl | 4-CF$_3$-6-Cl | O | 127-129 |

[Chemical formula 21]

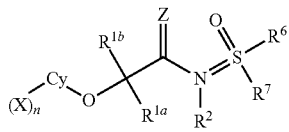

(c)

TABLE 5

| No. | $R^{1a}$ | $R^{1b}$ | $R^6$ | $R^7$ | Cy | $(X)n$ | Z | Melting Point °C. |
|---|---|---|---|---|---|---|---|---|
| 3-1 | Et | H | Me | Ph | Ph | 3,5-Cl$_2$ | O | 72-74 |
| 3-2 | Et | H | Me | Ph | Quinolin-6-yl | — | O | * |
| 3-3 | SMe | H | Me | Ph | Ph | 3,5-Cl$_2$ | O | * |

Among the compounds shown in TABLES 1-3, the melting point was measured for some of the compounds and described in the tables. $^1$H-NMR (CDCl$_3$) or infraction index was measured for the oil-form compounds and amorphous compounds (the compounds marked with * described in the tables). The measurement results are shown below.

1-4: $^1$H-NMR (CDCl$_3$) 8.67(br, 1H), 8.47-8.45(m, 1H), 7.69(dt, 1H), 7.33(d, 1H), 7.17(dd, 1H), 7.08(s, 2H), 4.40(dd, 1H), 2.03-1.98(m, 2H), 1.73(s, 3H), 1.69(s, 3H), 1.04(t, 3H)

1-16: refraction index 20.7° C. 1.5767

1-17: refraction index 20.7° C. 1.5985

1-20: refraction index 20.6° C. 1.5349

2-4: $^1$H-NMR (CDCl$_3$) 8.95(br, 1H), 8.72(s, 1H), 8.55(d, 1H), 8.03(d, 1H), 7.78-7.68(m, 2H), 7.38-7.19(m, 3H), 5.42(s, 1H), 3.56(s, 3H), 1.80(s, 3H), 1.75(s, 3H)

2-5: $^1$H-NMR (CDCl$_3$) 8.46-8.45(m, 2H), 7.77(dd, 1H), 7.68 (ddd, 1H), 7.36(d, 1H), 7.27(d, 1H), 7.16(ddd, 1H), 7.36 (dd, 1H), 7.10(d, 1H), 5.44(dd, 1H), 2.15-1.99(m, 2H), 1.74(s, 3H), 1.70(s, 3H), 1.04(t, 3H)

2-11: refraction index 20.8° C. 1.5748

3-2: $^1$H-NMR (CDCl$_3$) 8.78(d, 1H), 8.03-8.00(m, 2H), 7.68(d, 1H), 7.60-7.43(m, 4H), 7.33-7.22(m, 2H), 7.10(d, 1H), 4.54(t, 1H), 3.16(s, 3H), 2.11-2.02(m, 2H), 1.13(t, 3H)

3-3: $^1$H-NMR (CDCl$_3$) 7.97-7.92(m, 2H), 7.70-7.58(m, 3H), 7.01-6.99(m, 3H), 5.54(s, 1H), 3.38(s, 3H), 2.22(s, 3H)

1-23: $^1$H-NMR (CDCl$_3$) 8.73(br, 1H), 8.50(d, 1H), 7.58-7.46(m, 7H), 7.10(s, 2H), 4.42(t, 1H), 2.10-1.98(m, 2H), 1.79(s, 3H), 1.75(s, 3H), 1.06(t, 3H)

1-24: refraction index 20.6° C. 1.5739

1-34: $^1$H-NMR (CDCl$_3$) 9.92(br, 1H), 8.71(d, 2H), 7.31(s, 2H), 7.20(t, 1H), 4.71(t, 1H), 2.26-1.91(m, 2H), 1.94(s, 3H), 1.92(s, 3H), 1.05(t, 3H)

1-35: $^1$H-NMR (CDCl$_3$) 9.28(br, 1H), 8.56(d, 1H), 7.72(dt, 1H), 7.40-7.06(m, 10H), 5.91(s, 1H), 1.74(s, 6H)

1-45: $^1$H-NMR (CDCl$_3$) 8.64(br, 1H), 8.22(d, 1H), 6.95-7.07(m, 5H), 6.68(q, 1H), 2.46(s, 3H), 1.69(d, 3H), 1.68(s, 6H)

2-17: refraction index 20.7° C. 1.5198

2-19: refraction index 20.4° C. 1.4943

2-21: $^1$H-NMR (CDCl$_3$) 8.70(d, 2H), 8.14(br, 1H), 7.18(t, 1H), 6.93(s, 2H), 2.13-1.91(m, 2H), 1.76(s, 6H), 1.57(s, 3H), 0.98(t, 3H)

2-24: $^1$H-NMR (CDCl$_3$) 8.65(br, 1H), 8.23(d, 1H), 7.10(d, 1H), 6.98(dd, 1H), 6.88(s, 2H), 4.51(t, 1H), 2.48(s, 3H), 2.11-1.99(m, 2H), 1.71(s, 3H), 1.66(s, 3H), 1.04(t, 3H)

Some preparation examples of the pest control agent according to the present invention are shown below. However, additives and addition ratios are not limited to the preparation examples, and can be modified over a wide range. Moreover, the term "parts" used in the preparation examples indicates "weight parts." The following are the preparation examples for agricultural and horticultural use.

Preparation Example 1(Wettable Powder)

| Compound of the present invention | 40 parts |
|---|---|
| Diatom earth | 53 parts |
| Fatty alcohol sulfate | 4 parts |
| Alkylnaphthalene sulfonate | 3 parts |

The foregoing was uniformly mixed and finely pulverized to obtain a wettable powder including 40% of active ingredient.

Preparation Example 2(Emulsion)

| Compound of the present invention | 30 parts |
|---|---|
| Xylene | 33 parts |
| Dimethylformamide | 30 parts |
| Polyoxyethylene alkylaryl ether | 7 parts |

The foregoing was mixed and dissolved to obtain an emulsion including 30% of active ingredient.

The following are the preparation examples for epidemic-prevention and animals.

Preparation Example 3(Granulated Powder)

| Compound of the present invention | 5 parts |
|---|---|
| Kaolin | 94 parts |
| White carbon | 1 part |

The compound of the present invention was dissolved in an organic solvent, and sprayed on a carrier, followed by evaporating the solvent under reduced pressure. This kind of granulated powder may be mixed with animal food.

Preparation Example 4(Impregnating Agent)

| Compound of the present invention | 0.1-1 parts |
|---|---|
| Peanut oil | balance |

The impregnating agent was filter-sterilized by a sterilizing filter after adjustment.

Preparation Example 5(Pour-on Agent)

| Compound of the present invention | 5 parts |
|---|---|
| Myristic acid ester | 10 parts |
| Isopropanol | balance |

Preparation Example 6(Spot-on Agent)

| Compound of the present invention | 10-15 parts |
|---|---|
| Palmitic acid ester | 10 parts |
| Isopropanol | balance |

Preparation Example 7(Spray-on Agent)

| Compound of the present invention | 1 part |
|---|---|
| Propylene glycol | 10 parts |
| Isopropanol | balance |

[Biological Examination]

The following test examples demonstrate that the compound of the present invention is useful as an active ingredient of acaricide.

Test Example 1

Efficacy Test Against *Tetranychus urticae*

Ten organic phosphorous-resistant adult female *Tetranychus urticae* acarus were inoculated onto the first leaves of a kidney bean plant planted in a No. 3 pot 7 to 10 days after germination. Next, an emulsion was prepared having the formula indicated in the aforementioned Preparation example 2. This emulsion was diluted with water to a compound concentration of 125 ppm after which the diluted liquids were sprayed onto the kidney bean plant. The kidney bean plant was then placed in a temperature-controlled room at a temperature of 25° C. and humidity of 65%. The life and death of the adult insects were investigated 3 days after the spraying. In addition, the development from eggs laid to adult was investigated 14 days after the spraying.

The aforementioned test was carried out on the emulsions containing the Compound Nos. 1-3, 1-4, 1-5, 1-6, 1-7, 1-13, 1-14, 1-15, 1-16, 1-17, 1-18, 1-23, 1-24, 1-25, 1-27, 1-28, 1-29, 1-30, 1-31, 1-32, 1-34, 1-37, 1-38, 1-39, 1-40, 1-43, 2-1, 2-2, 2-3, 2-4, 2-6, 2-7, 2-10, 2-11, 2-12, 2-15, 2-16, 2-22, 2-23, 2-24, 2-25, and 2-28. As a result, the insect mortality rates after 3 days and 10 days for all of the compounds were 90% or higher.

Test Example 2

Efficacy Test Against *Panonychus citri*

Eight adult female *Panonychus citri* acarus from Kanagawa Prefecture were inoculated onto a mandarin orange leaf placed in a Petri dish. Next, an emulsion was prepared having the formula indicated in the aforementioned Preparation example 2. This emulsion was diluted with water to a compound concentration of 125 ppm after which the diluted liquids were sprayed onto the mandarin orange leaf with a rotary spraying tower. The mandarin orange leaf was then placed in a temperature-controlled room at a temperature of 25° C. and a humidity of 65%. The life and death of the adult insects were investigated 3 days after the spraying. In addition, the development from eggs laid to adult was investigated 10 days after the spraying.

The aforementioned test was carried out on the emulsions containing the Compound Nos. 1-1, 1-3, 1-4, 1-5, 1-6, 1-7, 1-8, 1-11, 1-13, 1-14, 1-16, 1-17, 1-18, 1-25, 1-28, 1-29, 1-30, 1-31, 1-34, 1-39, 1-40, 1-41, 1-42, 1-43, 2-1, 2-2, 2-3, 2-6, 2-7, 2-11, 2-16, 2-24, 2-25, and 2-28. As a result, the insect mortality rates after 3 days and 10 days for all of the compounds were 90% or higher.

Test Example 3

Efficacy Test Against *Panonychus citri*

Eight acaricide-resistant adult female *Panonychus citri* acarus from Wakayama Prefecture were inoculated onto a mandarin orange leaf placed in a Petri dish. Next, an emulsion was prepared having the formula indicated in the aforementioned Preparation example 2. This emulsion was diluted with water to a compound concentration of 125 ppm after which the diluted liquids were sprayed onto the mandarin orange leaf with a rotary spraying tower. The mandarin orange leaf was then placed in a temperature-controlled room at a temperature of 25° C. and a humidity of 65%. The life and death of the adult insects were investigated 3 days after the spraying. In addition, the development from eggs laid to adult was investigated 10 days after the spraying.

The aforementioned test was carried out on the emulsions containing the Compound Nos. 1-1, 1-4, 1-7, 1-14, 1-17, 1-18, and 1-34. As a result, the insect mortality rates after 3 days and 10 days for all of the compounds were 90% or higher.

Test Example 4

Efficacy Test Against *Tetranychus kanzawai*

Ten adult female *Tetranychus kanzawai* acarus from Okayama Prefecture were inoculated onto the first leaves of a kidney bean plant planted in a No. 3 pot 7 to 10 days after germination. Next, an emulsion was prepared having the formula indicated in the aforementioned Preparation example 2. This emulsion was diluted with water to a compound concentration of 500 ppm or 125 ppm after which the diluted liquids were sprayed onto the kidney bean plant. The kidney bean plant was then placed in a temperature-controlled room at a temperature of 25° C. and humidity of 65%. The life and death of the adult insects were investigated 3 days after the spraying. In addition, the development from eggs laid to adult was investigated 14 days after the spraying.

The aforementioned test was carried out on the emulsion containing the Compound No. 1-1 at 500 ppm. As a result, the insect mortality rates after 3 days and 14 days for the compound were 90% or higher.

In addition, the aforementioned test was carried out on the emulsions containing the Compound Nos. 1-3, 1-4, 1-5, 1-6, 1-7, 1-8, 1-9, 1-10, 1-11, 1-13, 1-14, 1-15, 1-16, 1-17, 1-18, 1-23, 1-24, 1-25, 1-27, 1-28, 1-29, 1-30, 1-31, 1-32, 1-34, 1-37, 1-38, 1-39, 1-40, 1-41, 1-42, 1-43, 1-45, 2-1, 2-2, 2-5, 2-6, 2-7, 2-8, 2-9, 2-10, 2-11, 2-12, 2-13, 2-15, 2-16, 2-22, 2-23, 2-24, 2-25, 2-28, 2-29, and 2-30 at 125 ppm. As a result, the insect mortality rates after 3 days and 14 days for all of the compounds were 90% or higher.

Test Example 5

Efficacy Test Against *Aculops pelekassi*

Twenty acaricide-resistant adult female *Aculops pelekassi* acarus were inoculated onto a mandarin orange leaf placed in a Petri dish. Next, an emulsion was prepared having the formula indicated in the aforementioned Preparation example 2. This emulsion was diluted with water to a compound concentration of 125 ppm after which the diluted liquids were sprayed onto the mandarin orange leaf with a rotary spraying tower. The mandarin orange leaf was then placed in a temperature-controlled room at a temperature of 25° C. and a humidity of 65%. The life and death of the adult insects were investigated 3 days after the spraying. The development from eggs laid to adult was investigated 10 days after the spraying.

The aforementioned test was carried out on the emulsion containing the Compound No. 1-14. As a result, the insect mortality rates after 3 days and 10 days for the compound were 90% or higher.

INDUSTRIAL APPLICABILITY

The aryloxyacetamide compound or salt thereof according to the present invention can protect agricultural crops against infection by harmful organisms. In addition, it also has hygiene applications. Particularly, the compound of the present invention is able to effectively reduce acarus.

The invention claimed is:

1. An aryloxyacetamide compound represented by formula (I), or salt thereof:

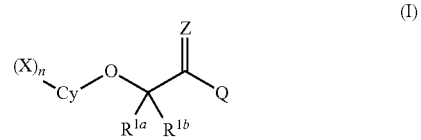

wherein

Cy represents a C6-10 aryl group, a 5-membered heteroaryl group, or a 6-membered heteroaryl group;

X is a substituent of Cy, and represents an unsubstituted or substituted C1-6 alkyl group, unsubstituted or substituted C3-8 cycloalkyl group, unsubstituted or substituted C2-6 alkenyl group, unsubstituted or substituted C2-6 alkynyl group, hydroxy group, unsubstituted or substituted C1-6 alkoxy group, amino group, unsubstituted or substituted C1-6 alkyl amino group, unsubstituted or substituted C1-7 acyl group, unsubstituted or substituted C1-6 alkoxycarbonyl group, unsubstituted or substituted C1-6 alkyl thio group, unsubstituted or substituted C1-6 alkyl sulfonyl group, unsubstituted or substituted C1-6 alkoxysulfonyl group, unsubstituted or substituted C6-10 aryl group, unsubstituted or substituted 5-membered heteroaryl group, unsubstituted or substitute 6-mebered heteroaryl group, unsubstituted or substituted hydroxyimino C1-6 alkyl group, nitro group, cyano group, or halogen atom;

n represents the number of X bonded with Cy and represents an integer of 0 to 5; when n is 2 to 5, Xs may be the same as or different from each other; when n is 2 to 5, Xs may bond to form a ring together with the carbon atoms or nitrogen atoms of Cy, which bond with Xs;

$R^{1a}$ represents an unsubstituted or substituted C1-6 alkyl group, unsubstituted or substituted C2-6 alkenyl group, unsubstituted or substituted C2-6 alkynyl group, unsubstituted or substituted C1-6 alkoxy group, or unsubstituted or substituted C1-6 alkyl thio group;

$R^{1b}$ represents a hydrogen atom, unsubstituted or substituted C1-6 alkyl group, unsubstituted or substituted C2-6 alkenyl group, or unsubstituted or substituted C2-6 alkynyl group;

$R^{1a}$ and $R^{1b}$ may bond to form a ring together with the carbon atom bonded thereto, or $R^{1a}$ and $R^{1b}$ may together form an ethylidene group or an isopropylidene group;

Z represents an oxygen atom or a sulfur atom;

Q represents a group represented by formula (II):

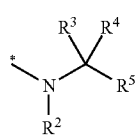

wherein
* represents bonding position;
$R^2$ represents a hydrogen atom, unsubstituted or substituted C1-6 alkyl group, unsubstituted or substituted C2-6 alkenyl group, unsubstituted or substituted C2-6 alkynyl group, unsubstituted or substituted C1-7 acyl group, or unsubstituted or substituted C1-6 alkoxycarbonyl group;
$R^3$ and $R^4$ independently represents an unsubstituted C1-6 alkyl group, a C1-6 haloalkyl group, a hydroxy C1-6 alkyl group, a C1-6 alkoxy C1-6 alkyl group, a C2-6 alkenyloxy C1-6 alkyl group, a heteroaryloxy C1-6 alkyl group, a C1-7 acyl group, a C1-7 acyloxy C1-6 alkyl group, a carboxyl group C1-6 alkyl group, a C1-6 alkoxycarbonyl C1-6 alkyl group, a C1-7 acyl amino C1-6 alkyl group, a C1-6 alkyl aminocarbonyl C1-6 alkyl group, a C1-6 alkoxycarbonyl amino C1-6 alkyl group, a C7-11 aralkyl group, a C6-10 aryl carbonyl amino C1-6 alkyl group, unsubstituted or substituted C2-6 alkenyl group, unsubstituted or substituted C2-6 alkynyl group, unsubstituted or substituted C6-10 aryl group, unsubstituted or substituted 5-membered heteroaryl group, or unsubstituted or substituted 6-membered heteroaryl group
$R^5$ represents an unsubstituted or substituted pyridyl group, unsubstituted or substituted pyrazinyl group unsubstituted or substituted pyrimidinyl group unsubstituted or substituted pyridazinyl group, unsubstituted or substituted triazinvl group, unsubstituted or substituted indolyl group, unsubstituted or substituted benzofuryl group, unsubstituted or substituted benzothienyl group, unsubstituted or substituted benzimidazolyl group, unsubstituted or substituted benzoxazolyl group, unsubstituted or substituted benzothiazolyl group, unsubstituted or substituted quinolyl group, unsubstituted or substituted isoquinolyl group, or unsubstituted or substituted quinoxalinyl group.

2. The aryloxyacetamide compound or salt thereof according to claim 1, wherein Cy represents a phenyl group, $R^{1b}$ represents a hydrogen atom. and Q represents a group represented by formula (II).

3. A pesticide comprising at least one selected from the group consisting of the aryloxyacetamide compound and salt thereof defined in claim 1 as an active ingredient.

4. An acaricide or insecticide comprising at least one selected from the group consisting of the aryloxyacetamide compound and salt thereof defined in claim 1 as an active ingredient.

5. An ectoparasite control agent comprising at least one selected from the group consisting of the aryloxyacetamide compound and salt thereof defined in claim 1 as an active ingredient.

6. A pesticide comprising at least one selected from the group consisting of the aryloxyacetamide compound and salt thereof defined in claim 2 as an active ingredient.

7. An acaricide or insecticide comprising at least one selected from the group consisting of the aryloxyacetamide compound and salt thereof defined in claim 2 as an active ingredient.

8. An ectoparasite control agent comprising at least one selected from the group consisting of the aryloxyacetamide compound and salt thereof defined in claim 2 as an active ingredient.

* * * * *